US012766315B2

(12) United States Patent
Rodenkirch et al.

(10) Patent No.: US 12,766,315 B2

(45) Date of Patent: Oct. 20, 2026

(54) TECHNIQUES FOR DETECTING HEARING LOSS AND FOR ENHANCING SENSORY PROCESSING BASED ON DETECTED HEARING LOSS

(71) Applicant: The Joan and Irwin Jacobs Technion-Cornell Institute, New York, NY (US)

(72) Inventors: Charles Rodenkirch, New York, NY (US); Michael Jigo, New York, NY (US)

(73) Assignee: The Joan and Irwin Jacobs Technion-Cornell Institute, New York, NY (US)

( * ) Notice: Subject to any disclaimer, the term of this patent is extended or adjusted under 35 U.S.C. 154(b) by 118 days.

(21) Appl. No.: 18/770,935

(22) Filed: Jul. 12, 2024

(65) Prior Publication Data

US 2025/0018190 A1 Jan. 16, 2025

Related U.S. Application Data

(60) Provisional application No. 63/513,256, filed on Jul. 12, 2023.

(51) Int. Cl.

*A61N 1/36* (2006.01)

*A61N 1/02* (2006.01)

(Continued)

(52) U.S. Cl.

CPC ............ *A61N 1/323* (2013.01); *A61N 1/025* (2013.01); *A61N 1/0456* (2013.01);

(Continued)

(58) Field of Classification Search

CPC .... A61N 1/025; A61N 1/0456; A61N 1/0492; A61N 1/0496; A61N 1/323;

(Continued)

(56) References Cited

U.S. PATENT DOCUMENTS

| | | | | |
|---|---|---|---|---|
| 8,620,450 | B2 | 12/2013 | Tockman et al. | |
| 11,245,996 | B1 * | 2/2022 | Hughes ................ | A61B 5/7455 |

(Continued)

FOREIGN PATENT DOCUMENTS

| | | | |
|---|---|---|---|
| EP | 2788079 | A1 | 10/2014 |
| WO | 2010088116 | A1 | 8/2010 |

(Continued)

OTHER PUBLICATIONS

Corrected International Search Report for PCT/IB2024/056807, dated Nov. 25, 2024. Searching Authority, Israel Patent Office, Jerusalem, Israel.

(Continued)

*Primary Examiner* — Jon Eric C Morales

(74) *Attorney, Agent, or Firm* — M&B IP Analysts, LLC

(57) ABSTRACT

Systems and methods for addressing hearing loss. A method includes monitoring volume conditions of at least one device in order to detect a plurality of changes in volume, wherein a volume of each of the at least one device is controlled by a subject; detecting hearing loss of the subject based on the monitored volume conditions; and applying a treatment to a subject when the hearing loss has been detected.

33 Claims, 26 Drawing Sheets

(51) Int. Cl.
*A61N 1/04* (2006.01)
*A61N 1/32* (2006.01)

(52) U.S. Cl.
CPC ......... *A61N 1/0492* (2013.01); *A61N 1/0496* (2013.01); *A61N 1/36025* (2013.01); *A61N 1/36031* (2017.08); *A61N 1/36034* (2017.08); *A61N 1/36036* (2017.08)

(58) Field of Classification Search
CPC ............ A61N 1/36025; A61N 1/36031; A61N 1/36034; A61N 1/36036; A61N 1/36053; A61N 1/36114
See application file for complete search history.

(56) References Cited

U.S. PATENT DOCUMENTS

| | | | |
|---|---|---|---|
| 2006/0015153 A1 | 1/2006 | Gliner et al. | |
| 2007/0027504 A1 | 2/2007 | Barrett et al. | |
| 2007/0076909 A1* | 4/2007 | Roeck | H04R 25/70 381/60 |
| 2012/0022617 A1* | 1/2012 | Tockman | A61N 1/36114 607/72 |
| 2012/0065702 A1 | 3/2012 | Arcot-Krishnamurthy et al. | |
| 2017/0087364 A1 | 3/2017 | Cartledge et al. | |
| 2017/0150282 A1 | 5/2017 | Mishra et al. | |
| 2021/0052884 A1 | 2/2021 | Jashek et al. | |
| 2023/0364428 A1 | 11/2023 | Fichman et al. | |
| 2024/0017074 A1 | 1/2024 | Mihajlovic et al. | |

FOREIGN PATENT DOCUMENTS

| | | |
|---|---|---|
| WO | 2016205872 A1 | 12/2016 |
| WO | 2022061070 A1 | 3/2022 |
| WO | 2022264540 A1 | 12/2022 |

OTHER PUBLICATIONS

Corrected Written Opinion of the Searching Authority for PCT/IB2024/056807, dated Nov. 25, 2024. Searching Authority, Israel Patent Office, Jerusalem, Israel.

Iliadou, Eleftheria, et al. “Profiling hearing aid users through big data explainable artificial intelligence techniques.” Frontiers in Neurology 13 (2022): 933940. Iliadou, Eleftheria, et al. Aug. 26, 2022 (Aug. 26, 2022).

International Search Report for PCT/IB2024/056778, dated Nov. 28, 2024. Searching Authority, Israel Patent Office, Jerusalem, Israel.

International Search Report for PCT/IB2024/056807, dated Nov. 19, 2024. Searching Authority, Israel Patent Office, Jerusalem, Israel.

International Search Report for PCT/IB2024/056812, dated Oct. 9, 2024. Searching Authority, Israel Patent Office, Jerusalem, Israel.

International Search Report for PCT/IB2024/056813, dated Nov. 25, 2024. Searching Authority, Israel Patent Office, Jerusalem, Israel.

Written Opinion of the Searching Authority for PCT/IB2024/056778, dated Nov. 28, 2024. Searching Authority, Israel Patent Office, Jerusalem, Israel.

Written Opinion of the Searching Authority for PCT/IB2024/056807, dated Nov. 19, 2024. Searching Authority, Israel Patent Office, Jerusalem, Israel.

Written Opinion of the Searching Authority for PCT/IB2024/056812, dated Oct. 9, 2024. Searching Authority, Israel Patent Office, Jerusalem, Israel.

Written Opinion of the Searching Authority for PCT/IB2024/056813, dated Nov. 25, 2024. Searching Authority, Israel Patent Office, Jerusalem, Israel.

* cited by examiner

TECHNIQUES FOR DETECTING HEARING LOSS AND FOR ENHANCING SENSORY PROCESSING BASED ON DETECTED HEARING LOSS

CROSS-REFERENCE TO RELATED APPLICATIONS

This application claims the benefit of U.S. Provisional Application No. 63/513,256 filed on Jul. 12, 2023, the contents of which are hereby incorporated by reference.

TECHNICAL FIELD

The present disclosure relates generally to detecting hearing loss, and more specifically to detecting hearing loss via monitoring volume settings of devices over time.

BACKGROUND

Impaired sensory processing is linked to a variety of negative effects on life. Examples include withdrawal from social situations, increased risk of falls or other accidents, and inability to live independently. Seniors often face these challenges and more as sensory processing declines with age. Aging both deteriorates sensory receptors such as eyes and ears, and impairs the brain's ability to process signals received from those receptors (i.e., central sensory processing). The combined effects of sensory loss may cause anxiety, depression, and accelerated onset of dementia.

In addition to aging, other individuals may experience impaired sensory processing. Individuals with sensory processing disorders such as attention deficit hyper disorder (ADHD) and dyslexia have been shown to be more likely to have impaired sensory processing. Moreover, fatigue, inattention, and concussions can all impair sensory processing. Athletes and other active individuals can therefore also experience impaired sensory processing. Decreased sensory acuity is linked with increased risk of injury and poor performance at work, school, and recreational activities.

Existing solutions for treating sensory loss in seniors such as glasses and hearing aids address deterioration of receptors. However, other these solutions do not address other potential causes of impaired sensory processing. Additionally, these solutions face challenges in improving sensory processing for individuals who do not demonstrate deteriorated receptors. Other existing solutions may include chemical or other pharmaceutical stimulants which can help improve sensory processing but have side effects such as cardiac damage, insomnia, anxiety, loss of appetite, and addiction. Further, nootropics and supplements may fail to provide the benefits advertised at best, and be actively harmful to consumers at worst.

New solutions for improving sensory processing would therefore be desirable.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for addressing hearing loss. The method comprises: monitoring volume conditions of at least one device in order to detect a plurality of changes in volume, wherein a volume of each of the at least one device is controlled by a subject; detecting hearing loss of the subject based on the monitored volume conditions; and applying a treatment to a subject when the hearing loss has been detected.

Certain embodiments disclosed herein also include a non-transitory computer readable medium having stored thereon causing a processing circuitry to execute a process, the process comprising: monitoring volume conditions of at least one device in order to detect a plurality of changes in volume, wherein a volume of each of the at least one device is controlled by a subject; detecting hearing loss of the subject based on the monitored volume conditions; and applying a treatment to a subject when the hearing loss has been detected.

Certain embodiments disclosed herein also include a system for addressing hearing loss. The system comprises: a processing circuitry; and a memory, the memory containing instructions that, when executed by the processing circuitry, configure the system to: monitor volume conditions of at least one device in order to detect a plurality of changes in volume, wherein a volume of each of the at least one device is controlled by a subject; detect hearing loss of the subject based on the monitored volume conditions; and apply a treatment to a subject when the hearing loss has been detected.

Certain embodiments disclosed herein include a method, non-transitory computer readable medium, or system as noted above or below, wherein applying the treatment to the subject includes sending a control signal to an audio modulator, wherein the control signal causes the audio modulator to alter an audio modulation for at least one of the at least one device based on the detected hearing loss.

Certain embodiments disclosed herein include a method, non-transitory computer readable medium, or system as noted above or below, wherein the control signal further causes the audio modulator to perform background noise suppression based on the detected hearing loss.

Certain embodiments disclosed herein include a method, non-transitory computer readable medium, or system as noted above or below, wherein the at least one device is at least one first device, wherein the monitored volume conditions for each device include a volume of a signal sent to a second device configured to modulate amplitude and a volume of a signal sent from the second device to a speaker.

Certain embodiments disclosed herein include a method, non-transitory computer readable medium, or system as noted above or below, wherein the volume conditions are monitored with respect to choices of volume made by the subject.

Certain embodiments disclosed herein include a method, non-transitory computer readable medium, or system as noted above or below, further including or being configured to perform the following step or steps: applying at least one machine learning model to at least a portion of the monitored volume conditions, wherein each machine learning model is trained using a respective set of training volume data for the subject Certain embodiments disclosed herein include a method, non-transitory computer readable medium, or system as noted above or below, wherein the at least one machine learning model includes a support vector machine.

Certain embodiments disclosed herein include a method, non-transitory computer readable medium, or system as noted above or below, wherein each of the at least one machine learning model corresponds to a respective device of the at least one device, wherein the respective set of training volume data used to train each of the at least one machine learning model is a set of volume data for the corresponding device of the machine learning model.

Certain embodiments disclosed herein include a method, non-transitory computer readable medium, or system as noted above or below, further including or being configured to perform the following step or steps: recording the monitored volume conditions with respect to a plurality of device types, wherein the hearing loss of the subject is detected based further on a type of device of each of the at least one device.

Certain embodiments disclosed herein include a method, non-transitory computer readable medium, or system as noted above or below, further including or being configured to perform the following step or steps: recording the monitored volume conditions with respect to a plurality of types of content being projected, wherein the hearing loss of the subject is detected based further on a type of content projected via each of the at least one device.

Certain embodiments disclosed herein include a method, non-transitory computer readable medium, or system as noted above or below, further including or being configured to perform the following step or steps: storing the monitored volume conditions in a storage which is accessible to a plurality of user devices of a plurality of subjects including the first subject, wherein the storage further stores volume conditions for the plurality of subjects, wherein the hearing loss is detected based on the volume conditions for the plurality of subjects.

Certain embodiments disclosed herein include a method, non-transitory computer readable medium, or system as noted above or below, further including or being configured to perform the following step or steps: separating the volume conditions into a plurality of time windows of equal length, wherein the volume conditions of each of the plurality of time windows include a plurality of volume values; and determining an average volume value for each of the plurality of time windows; determining that the average volume value for at least a threshold number of consecutive time windows among the plurality of time windows is more than a threshold value above a baseline volume value, wherein the hearing loss is detected based on the determination that the average volume value for at least a threshold number of consecutive time windows among the plurality of time windows is more than a threshold value above a baseline volume value.

Certain embodiments disclosed herein include a method, non-transitory computer readable medium, or system as noted above or below, wherein applying the treatment to the subject includes applying an electrical current in order to stimulate a vagus nerve of the subject.

Certain embodiments disclosed herein include a method, non-transitory computer readable medium, or system as noted above or below, further including or being configured to perform the following step or steps: determining a degree of stimulation for the vagus nerve of the subject based on a degree of the hearing loss, wherein the electrical current is applied based on the determined degree of stimulation.

Certain embodiments disclosed herein include a method, non-transitory computer readable medium, or system as noted above or below, further including or being configured to perform the following step or steps: sending control signals in order to control the electrical current delivered from a power source to a pair of electrodes in a continuous biphasic stimulation pattern, wherein the pair of electrodes is spaced such that the pair of electrodes applies a current to stimulate a vagus nerve of a subject using a current delivered from the power source when the pair of electrodes is disposed along a carotid triangle of a neck of the subject.

Certain embodiments disclosed herein include a method, non-transitory computer readable medium, or system as noted above or below, wherein an interelectrode distance between the pair of electrodes is between 4 and 5 centimeters.

Certain embodiments disclosed herein include a method, non-transitory computer readable medium, or system as noted above or below, wherein the interelectrode distance is 4 centimeters.

Certain embodiments disclosed herein include a method, non-transitory computer readable medium, or system as noted above or below, wherein the continuous biphasic stimulation pattern utilizes a plurality of pulses, wherein each pulse is less than one millisecond in length.

Certain embodiments disclosed herein include a method, non-transitory computer readable medium, or system as noted above or below, wherein the continuous stimulation pattern includes a plurality of pulses with a square biphasic waveform having two phases.

Certain embodiments disclosed herein include a method, non-transitory computer readable medium, or system as noted above or below, wherein each of the two phases of the square biphasic waveform is 100 milliseconds in length.

Certain embodiments disclosed herein include a method, non-transitory computer readable medium, or system as noted above or below, wherein the continuous biphasic stimulation pattern utilizes a plurality of pulses delivered at a frequency between 15 and 60 Hertz.

Certain embodiments disclosed herein include a method, non-transitory computer readable medium, or system as noted above or below, wherein the plurality of pulses is delivered at a frequency of 30 Hertz.

Certain embodiments disclosed herein include a method, non-transitory computer readable medium, or system as noted above or below, wherein the plurality of pulses is delivered at a frequency of 45 Hertz.

Certain embodiments disclosed herein include a method, non-transitory computer readable medium, or system as noted above or below, wherein the continuous biphasic stimulation pattern includes an asymmetric biphasic waveform.

Certain embodiments disclosed herein include a method, non-transitory computer readable medium, or system as noted above or below, wherein the electrical current delivered from the power source of the pair of electrodes in the biphasic stimulation pattern is initially delivered at a first current level and then incrementally increased from the first current level to a second current level.

Certain embodiments disclosed herein include a method, non-transitory computer readable medium, or system as noted above or below, wherein the first current level is 5 milliamps.

Certain embodiments disclosed herein include a method, non-transitory computer readable medium, or system as noted above or below, wherein the second current level is at most 60 milliamps.

Certain embodiments disclosed herein include a method, non-transitory computer readable medium, or system as noted above or below, further including or being configured to perform the following step or steps: sending control signals in order to control the electrical current delivered from a power source to a pair of electrodes in a continuous biphasic stimulation pattern, wherein the pair of electrodes is spaced such that the pair of electrodes applies a current to stimulate a vagus nerve of a subject using a current delivered from the power source when the pair of electrodes is disposed within a cymba concha of an ear the subject.

Certain embodiments disclosed herein include a method, non-transitory computer readable medium, or system as noted above or below, wherein the continuous biphasic stimulation pattern has a stimulation intensity between 0.5 and 4 milliamps.

Certain embodiments disclosed herein include a method, non-transitory computer readable medium, or system as noted above or below, wherein the stimulation intensity of the continuous biphasic stimulation pattern is 2 milliamps.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
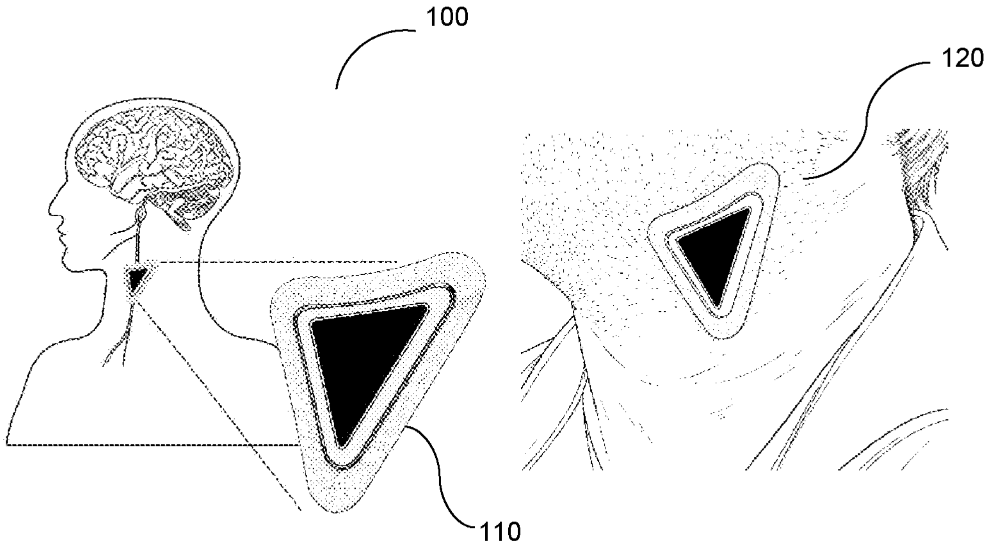
FIG. 1 is a diagram illustrating a device placed on a carotid triangle according to an embodiment.

It has been identified that senses of a subject such as vision, hearing, and touch, are more accurate when the subject is attentive and alert. When highly attentive, the brain activates neural circuitry in ways that optimize how sensory information is encoded and processed. This optimized sensory processing removes noise and may increase the accuracy and detail of sensory information, which allows for more accurate perception. Accordingly, various disclosed embodiments allow a subject (e.g., a subject wearing a wearable device) to activate this neural circuitry on demand in order to enhance sensory acuity and reduce misperceptions.

In this regard, it has been identified that, after sensory information is encoded by receptors (e.g., eyes, ears, skin), the sensory information enters the brain as a pattern of neural activity encoded as a neural signal. This signal is then processed through multiple brain regions before it is perceived during sensory processing, which lets brain regions along this pathway such as, but not limited to, the thalamus, to influence how the world is perceived. Perceptual acuity is therefore dependent upon high-fidelity, accurate sensory processing. As thalamic processing is a biological process, suboptimal conditions (e.g., brain states, neurochemical levels) may introduce noise or dysfunction in neural circuits that degrades the sensory information processed, thereby resulting in degraded acuity of perceived sensory content.

It has further been identified, via testing on subjects such as rats, that steady activation of the locus coeruleus-norepinephrine (LC-NE) system can cause a steady increase in NE concentration in the thalamus that enables optimization of intrathalamic dynamics for more accurate and detailed sensory processing. It has been identified that such an NE-enhanced sensory processing state can translate to enhanced sensory acuity as evidenced by improved performance on sensory discrimination tests. Moreover, it is noted that the function of neuromodulatory systems are similar in humans and rodents such that it has been identified that the applications of these findings (including the various disclosed embodiments) may be applied to humans and potentially other animals as well.

On a related note, it has also been identified that the increased NE levels used to improve sensory processing alter the response properties of thalamic neurons encoding sensory information in a manner that reduces the influence of calcium t-channels (membrane channels in neurons that influence electrical potential and therefore spiking response) responsible for burst firing. It has been identified that burst firing, and influence of calcium t-channels, can impair the ability of neurons to accurately encode details of sensory stimuli such that the process of burst firing tends to decrease sensory acuity.

Further, it has been identified that direct activation of the LC may be dangerous in humans due to the LC's location deep in the brainstem near regions involved with regulation of the autonomic nervous system that controls critical involuntary functions. However, it has been identified that vagus nerve stimulation (VNS) can be utilized to activate the LC. The vagus nerve innervates the nucleus tractus solitarius and provides excitatory input. When VNS is applied, the nucleus of the solitary tract (NTS) is activated, which in turn innervates and activates the LC. Moreover, it has been further identified that certain patterns of VNS particularly demonstrate beneficial effects on sensory processing similar to that seen with LC stimulation such that these patterns may be leveraged, in accordance with various disclosed embodiments, in order to achieve activation of the LC-NE system to produce comparable or otherwise similar effects to direct activation of the LC, thereby allowing for utilizing LC activation to improve sensory processing while avoiding certain harmful effects of implants or energy targeted for direct LC activation.

In this regard, it has further been identified that certain VNS patterns may be utilized in order to provide a benefit to sensory processing, Some such stimulation patterns may include fully continuous electrical waveforms with no quiescent periods (e.g., continuous alternating current), and other such stimulation patterns may include transient stimulation events with quiescent intervals in between (e.g., pulsed stimulation with quiescent inter-pulse-intervals). Further, either type of those waveforms can be either delivered nonstop or can be delivered with a duty-cycle stimulation pattern (i.e., a stimulation pattern including multiple pulses or a continuous waveform) being repeatedly delivered for some time period (on cycle) and then not delivered for another time period (off cycle), with this cycle repeating continuously. Stimulation patterns can also be modulated over time by changing frequency or amplitude of current.

In this regard, it has been identified that stimulation patterns which have duty cycles that create quiescent periods greater than about 10 seconds tend to create a fluctuating influence on NE levels in the brain and, in turn, a fluctuating influence on sensory processing which may yield suboptimal results. It has further been identified that stimulation patterns which contain quiescent periods longer than about 100 milliseconds may result in a continuous sensation of electrical current at the skin. In at least some implementations, such a continuous sensation of electrical current may be desirable to avoid, for example, to avoid potential distractions caused by such stimulation. It has yet further been identified that a stimulation pattern with less than about 40 ms of quiescent time between stimulation pulses may result in desensitization of the skin within about 5 minutes of use, with some subjects experiencing desensitization within 1 minute and others experiencing desensitization up to 10 minutes after stimulation begins. This may allow for reducing any sensation at the interface site between the skin and the stimulating device producing the transcutaneous electrical field. Therefore, an uninterrupted tonic stimulation pattern may provide better results for at least some implementations. More specifically, an uninterrupted tonic stimulation pattern may mimic the continuous tonic activation of the LC-NE system that occurs naturally during increased attention or arousal, and may therefore improve effects on sensory perception.

It has also been identified that the LC-NE system may modulate sensory processing of visual and auditory modalities in a similar manner. More specifically, it has been identified that increased attention and NE levels correlated with reduced bursting activity in neurons processing visual and auditory information (e.g., in thalamus, cortex, etc.). Accordingly, it has been identified that increases in forebrain NE concentration, and suppression of calcium t-channel bursting activity, may be utilized to enhance thalamic information processing and transmission. It has therefore been determined that the NE system may be able to optimize sensory perception.

To this end, various disclosed embodiments leverage these discoveries regarding the effects of LC-NE activation on sensory processing and the use of VNS to activate the LC in a manner which improves safety as compared to, for example, direct LC stimulation. At least some disclosed embodiments utilize patterns of VNS stimulation which have been discovered to yield particularly optimal sensory processing improvements. In particular, various disclosed embodiments utilize an uninterrupted tonic pattern of VNS which has been identified to allow for enhanced sensory processing.

In particular, various disclosed embodiments may use or include an externally worn, transcutaneous cervical vagus nerve stimulation (nVNS) patch. Such a patch may be conveniently removable in order to allow users to utilize the patch during specific times, for example, when participating in sports, when operating in dangerous conditions, or otherwise when it is desirable to improve sensory processing. This patch may also, in accordance with various disclosed embodiments, be designed to be fully noninvasive and to deliver electrical current to the vagus nerve through the skin via flat electrodes which may rest above where the vagus nerve runs through the neck. This patch may also have an adhesive layer which holds the device and electrodes in contact with the skin. Accordingly, the disclosed nVNS techniques and devices allow for providing a safe and effective means of inducing neuromodulation which can be activated and deactivated on-demand.

The disclosed embodiments may therefore be utilized in different implementations which may require sensory processing improvements or otherwise for which sensory processing improvements may be desirable. In particular, various disclosed embodiments may aid individuals with neurodegenerative disorders which affect sensory processing such as, but not limited to, Alzheimer's disease, Parkinson's, age-related sensory loss, shift-work syndrome, insomnia, and the like. More specifically, various disclosed embodiments may be utilized in order to treat patients with these impairments. Additionally, individuals with disorders such as ADHD and dyslexia may be treated in order to mitigate the effects of these disorders on sensory processing.

In addition to treating individuals having certain disorders, various disclosed embodiments may have applicability in contexts such as sports, gaming, or other contexts where enhanced sensory processing might be desirable including, but not limited to, students, artists, individuals enjoying sensorial content, military, and the like. As a non-limiting example, athletes playing a physical sport or e-sport may benefit from improved sensory processing which may allow them to more accurately perceive visual, auditory, and tactile feedback. This, in turn, may reduce misperceptions, miscommunications, clumsy hands, combinations thereof, and the like, that could impair performance. Likewise, individuals performing tasks which are inherently dangerous and require sharp sensory processing (as misperceptions may result in costly human error) may benefit from various disclosed embodiments.

FIG. 1 is a diagram 100 illustrating a device placed on a carotid triangle according to an embodiment. The diagram 100 illustrates a device 110 in the form of a triangular patch which may be disposed on a neck 120 of a user in accordance with various disclosed embodiments. More specifically, in an embodiment, the device 110 is aligned above the carotid artery of the neck because the vagus nerve runs adjacent and parallel with the carotid artery underneath the carotid triangle of the neck. In accordance with various disclosed embodiments, the device 110 is disposed on a carotid triangle of the neck 120 of the user. In the embodiment depicted in FIG. 1, the device 110 may be placed on a user non-invasively, i.e., without needing to pierce the skin of the neck 120 of the user or otherwise implanting the device 110 underneath the skin of the neck 120. Thus, the disclosed embodiments may allow for improving sensory processing non-invasively.

Figure 2:
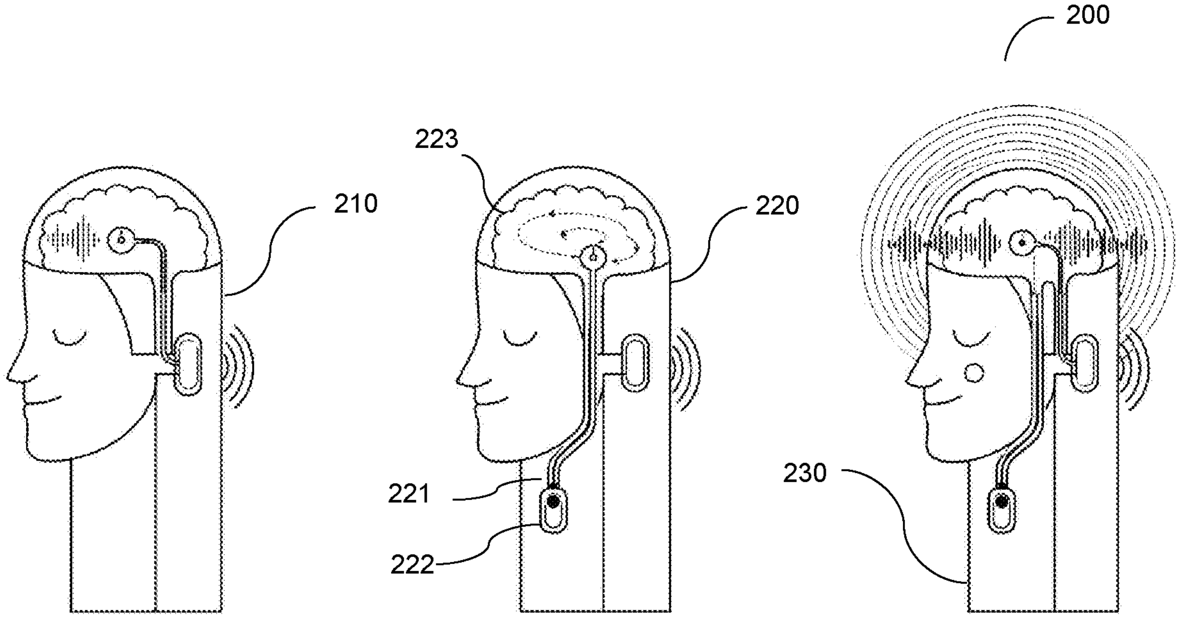
FIG. 2 is mechanism of action diagram illustrating vagus nerve stimulation utilized to describe various disclosed embodiments.

FIG. 2 is a mechanism of action diagram 200 illustrating vagus nerve stimulation utilized to describe various disclosed embodiments. The diagram 200 illustrates certain aspects in accordance with various disclosed embodiments. More specifically, the diagram 200 illustrates conversion 210 of sound into a neural signal by the ear, which is then processed by the brain before perception occurs. The diagram 200 also illustrates stimulation 220 of a vagus nerve 221 via a device 222 and demonstrates how stimulation of the vagus nerve 221 causes norepinephrine levels to increase in regions of a brain 223 which process auditory information. The device 222 may be a device configured in accordance with one or more disclosed embodiments. Further illustrated are effects 230 of the resulting increased norepinephrine levels resulting in enhanced sensory processing, which in turn results in a clearer perception of the sound.

In accordance with at least some disclosed embodiments, stimulation may be targeted at a section of the vagus nerve located under the carotid triangle. To this end, in an embodiment, the device 222 is disposed on a left side of the neck. As discussed further below with respect to FIG. 3, the device 222 may include a pair of electrodes (e.g., hydrogel electrodes) to facilitate delivery of electric energy targeting the vagus nerve 221 as it runs under the location of the carotid triangle. In at least some embodiments, the device 222 does not extend above the neck onto the jaw.

In accordance with various disclosed embodiments, the device 222 utilizes directed energy targeted at certain tissues (e.g., neural, organ, muscles, etc.). The directed energy may be delivered with specific patterns (e.g., waveform, intensity, frequency, etc.) in order to evoke certain changes in neural activity, behavior, and cognition. To this end, the device 222 may be realized as, for example but not limited to, a neural stimulation patch adapted to activate neural circuitry (e.g., the norepinephrine system via stimulation of the vagus nerve 221) that causes enhancement of central sensory processing. Specifically, the enhanced central sensory processing may improve acuity of any of vision, hearing, touch, and the like. In at least some implementations, the enhanced sensory processing may be realized instantly after stimulation begins and may continue until the device 222 is removed. As noted above, vagus nerve stimulation may allow for enhancing sensory processing while minimizing or avoiding side effects.

In at least some embodiments, the device 222 may be realized as or using an adhesive patch. In some implementations, the entire patch (i.e., the entire device 222) may be disposable. In other implementations, some components of the device 222 (e.g., a microchip, not shown in FIG. 2) are durable and components such as electrodes and batteries are replaceable. In an embodiment, the device 222 has dimensions between 5 to 6 centimeters tall, 2 to 3 centimeters wide, and thickness less than 0.5 centimeters.

Figure 3:
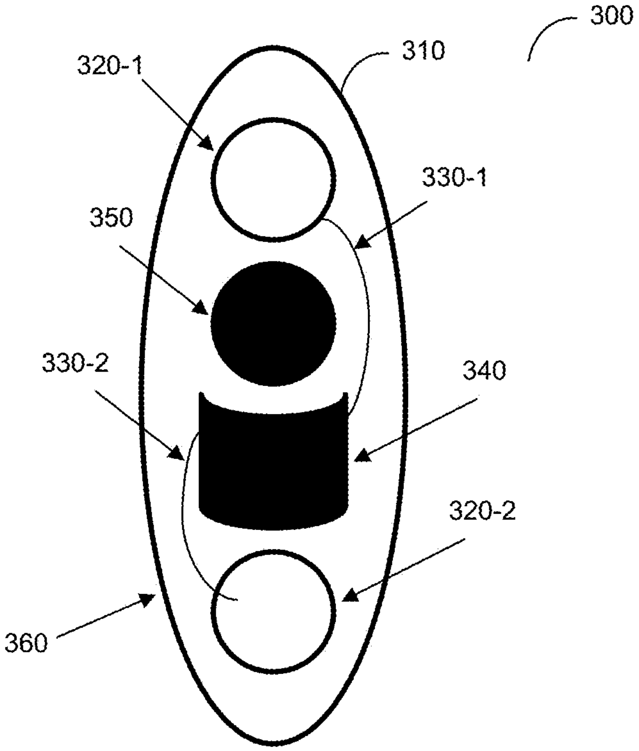
FIG. 3 is a schematic diagram illustrating components of a device in accordance with various disclosed embodiments.

FIG. 3 is a schematic diagram illustrating components of a device 300 in accordance with various disclosed embodiments.

As depicted in FIG. 3, an outer edge 310 of the device 300 may be designed with a shape that may vary on the use case. The example shape of the outer edge 310 depicted in FIG. 3 may allow for minimizing the size of the device 300, but other shapes may be equally utilized in accordance with various disclosed embodiments. For example, in some embodiments, the device 300 may be triangular as depicted in FIG. 1. Such a triangular shape may aid a user in correctly aligning placement of the device 300 with respect to a carotid triangle. The outer edge 310 may be, but is not limited to, around 0.5 centimeters thick.

The device 300 includes a pair of electrodes 320-1 and 320-2. In an embodiment, each of the electrodes 320-1 and 320-2 is a gel electrode. In a further embodiment, each electrode 320-1 and 320-2 has a diameter of 2 centimeters. In yet a further embodiment, a distance between center points of the electrodes 320-1 and 320-2 is 4 centimeters. In another embodiment, the distance between such center points is between 4 and 5 centimeters.

In this regard, it is noted that optimal interelectrode distance in at least some embodiments is based on the height of the carotid triangle of a given user. More specifically, electrodes which are placed outside of the carotid triangle may face challenges in optimally penetrating the vagus nerve with current due to increased muscle between the skin and the target nerve at locations outside of the carotid triangle. It has been identified that a distance between 4 and 5 centimeters between electrodes may allow for optimizing penetration of current in accordance with various disclosed embodiments. Moreover the shape of the electrodes may be selected in order to maximize surface area, distance between center points, or both.

The electrodes 320-1 and 320-2 are connected via respective wires 330-1 and 330-2 to a circuit board 340 such as, but not limited to, a printed circuit board. As depicted in FIG. 3, the circuit board 340 is shaped in order to partially surround a battery 350, although other shapes may be equally utilized in at least some other embodiments. In some implementations, the circuit board 340 and the battery 350 may be stacked on top of each other. In an embodiment, the circuit board has a surface area of around 2 square centimeters. In a further embodiment, the circuit board is 1 millimeter thick. In yet a further embodiment, the circuit board is opaque. In yet a further embodiment, the circuit board is transparent. In yet a further embodiment, the circuit board is flexible. In some embodiments, the electrodes 320-1 and 320-2 are surrounded by an edge 360 of the device 300 which extends at least 1 centimeter beyond the outer boundary of the electrodes 320-1 and 320-2.

In this regard, it has been identified that maintaining a minimal surface area for the electrodes may be utilized to ensure that the current density during stimulation does not increase to a level where discomfort or injury would occur. It has further been identified that a surface area of around at least 2 square centimeters allows for delivering a sufficient current to enhance sensory processing via vagus nerve stimulation while minimizing or avoiding any discomfort or injury. In other embodiments, electrodes with larger surface areas may be utilized. In that regard, it is noted that larger electrodes may allow for minimizing cutaneous pain due to reduced current density at skin, and may therefore be particularly suitable for deeper nerve stimulation and/or constant recruitment.

It has further been identified that conductive hydrogel electrode coatings may be utilized to improve the performance of bionic devices, which may utilize lower amounts of energy than certain metal electrodes as well as which may exhibit better biocompatibility and adhesive properties. Thus, in at least some embodiments, hydrogel electrodes are utilized. In other embodiments, other materials with suitable conductivity to provide vagus nerve stimulation in order to realize enhanced sensory processing may be utilized (e.g., carbon/rubber, silver/silver chloride, stainless steel, nickel, gold, etc.).

Figure 4:
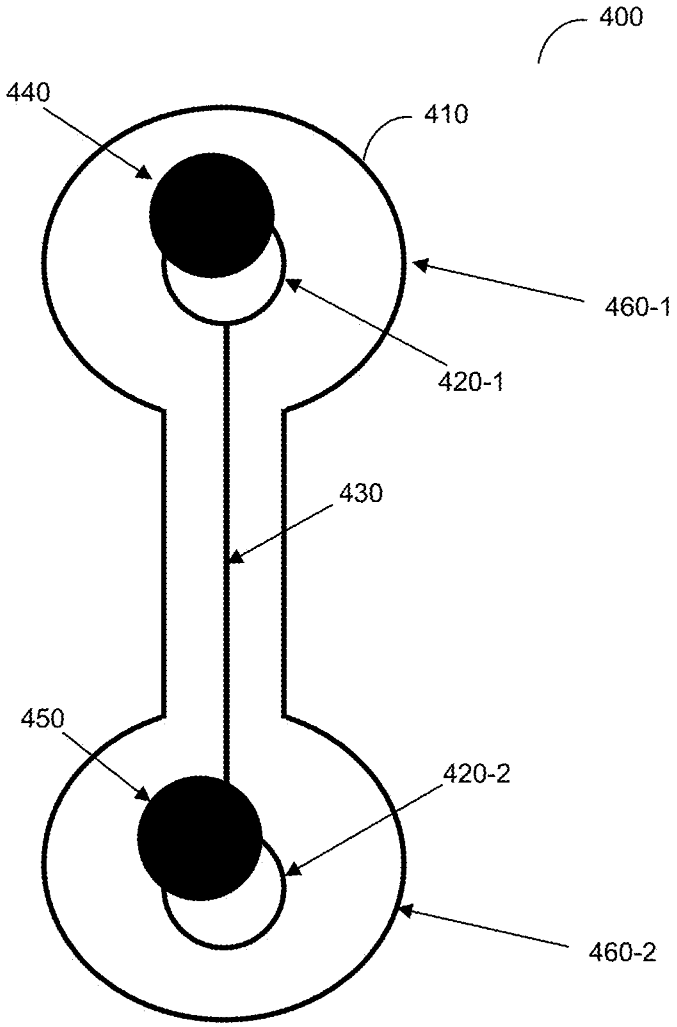
FIG. 4 is a diagram illustrating a dumbbell-shaped design of a device according to an embodiment.
Figure 5:
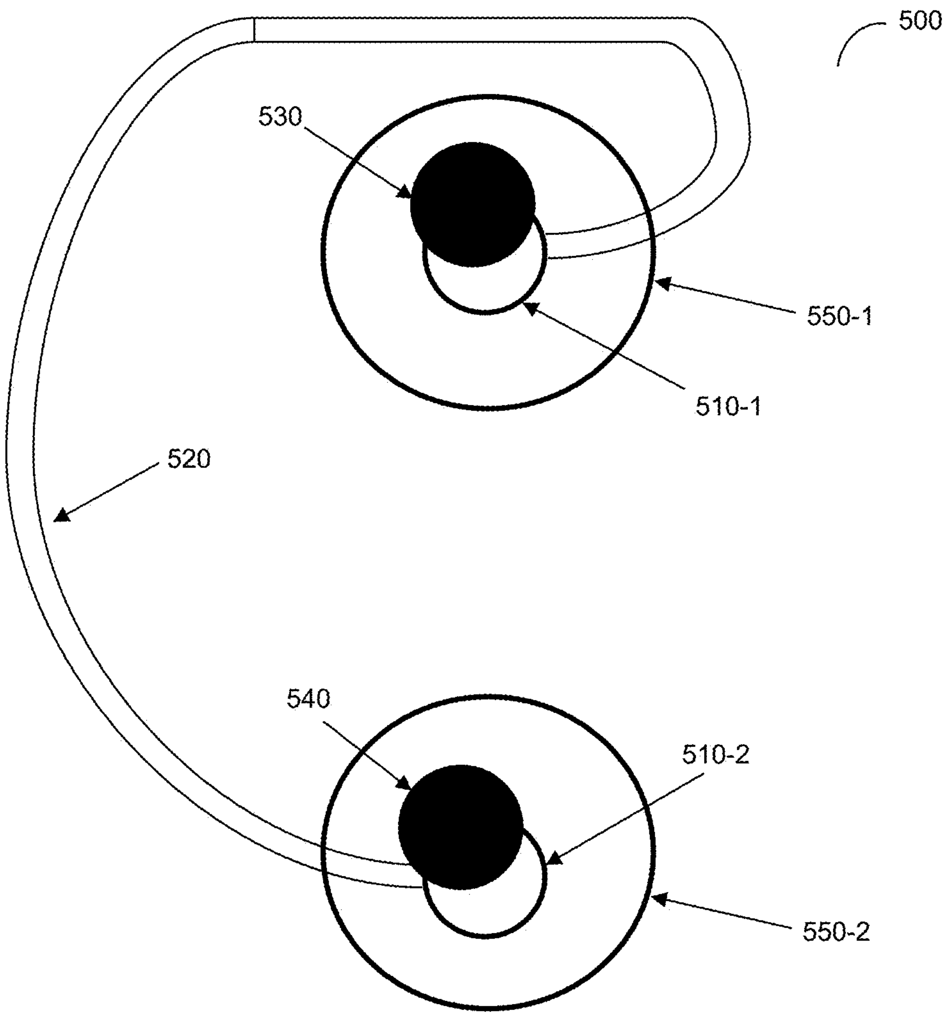
FIG. 5 is a diagram illustrating a necklace-shaped design of a device according to an embodiment.

The wires 330-1 and 330-2 may be or may include, but are not limited to, conductive wires, traces, and the like. In some embodiments, wires may not be utilized for components which are connected directly (e.g., via solder contact points). Examples of such direct connections are depicted in FIGS. 4 and 5, where electrodes are connected directly to circuit boards and batteries, respectively.

The battery 350 is connected to the circuit board 340, either via direct contact or via a wire (not shown in FIG. 3). To this end, the battery 350 may be stacked on top of the circuit board 340 (not shown) or placed side-by-side (as shown). In an embodiment, the battery has a diameter of about 2 centimeters and a thickness of about 1 millimeter. In a further embodiment, the battery is opaque. In an example implementation, the battery may be a coin cell battery (e.g., lithium ion). In yet a further embodiment, the battery may be transparent. In yet a further embodiment, the battery may be flexible.

The circuit board 340 is adapted to convert a voltage differential from the battery 350 into pulsed waveform patterns as described herein. In an embodiment, a timer integrated circuit is utilized for pulse generation. In another embodiment, an operational amplifier is used for current delivery. In some implementations, a microcontroller may be used; in other implementations, a less complicated (and therefore less power consuming) chip may be utilized (e.g., an application-specific integrated circuit). In some implementations, an aperture in a chip (not shown) of the circuit board 340 may be defined in order to allow for placement of the battery therein.

The various components shown in FIG. 3 may be encased or otherwise enclosed in a film (not depicted in FIG. 3) used to realize the device 300 as a patch. In some implementations, the film may be transparent in order to allow natural skin color to show through the film. Such a film may be around 0.2 millimeters thick. Moreover, the film may be made of materials such as, but not limited to, silicone, plastic, resin, epoxy, thin-film laminates, metals, sprayable conformal coatings (e.g., parylene, silicone dioxide, polytetrafluoroethylene, acrylic, epoxy, etc.) combinations thereof, and the like. The film, in at least some embodiments, may be used to form a water-resistant enclosure. In other embodiments a water-resistant film is applied directly to all electrical sub-components.

FIG. 4 is a diagram illustrating a dumbbell-shaped design of a device 400 according to an embodiment.

As depicted in FIG. 4, a pair of electrodes 420-1 and 420-2 are connected via a wire 430. In the embodiment shown in FIG. 4, a circuit board 440 is stacked on top of one of the electrodes 420-1 and a battery 450 is stacked on top of another of the electrodes 420-2. Such a stacking design may reduce the area of the device 400 that is opaque (e.g., allowing more space to be occupied by a transparent film) in exchange for increased thickness of the device 400.

In an embodiment, the electrodes 420-1 and 420-2 each have a diameter of 2 centimeters and a thickness of 1 millimeter. The circuit board 440 may be opaque and, in an embodiment, has a surface area equal to or greater than 3 centimeters. The battery 450 maybe opaque and, in an embodiment, have a thickness of 1.6 millimeters and a diameter of 2 centimeters. In some embodiments, the electrodes 420-1 and 420-2 are surrounded by edges 460-1 and 460-2, respectively, which extend at least 1 centimeter beyond the outer boundary of the respective electrodes 420-1 and 420-2.

FIG. 5 is a diagram illustrating a necklace-shaped design of a device 500 according to an embodiment. In this regard, it is noted that a device 500 which wraps around a user's neck may be desirable in order to demonstrate a natural-looking appearance like neckwear such as necklaces or scarves, or to be covered by such neckwear. The embodiment depicted in FIG. 5 may provide such a natural-looking or convenient to cover appearance.

As depicted in FIG. 5, electrodes 510-1 and 510-2 are connected via a wire 520 designed to wrap around a neck (not shown in FIG. 5). To this end, the wire 520 may be long enough (e.g., between 10 and 20 inches) in order to allow the wire to wrap around a user's neck. Moreover, in some implementations, the wire may be made of metal in order to appear more like a necklace. A circuit board 530 and a battery 540 may be stacked on top of the electrodes 510-1 and 510-2, respectively.

In an embodiment, the electrodes 510-1 and 510-2 each have a diameter of 2 centimeters and a thickness of 1 millimeter. The circuit board 530 may be opaque and, in an embodiment, has a surface area equal to or greater than 3 centimeters. The battery 540 maybe opaque and, in an embodiment, have a thickness of 1.6 millimeters and a diameter of 2 centimeters. The electrodes 510-1 and 510-2 may be surrounded by edges 550-1 and 550-2, respectively, which extend at least 1 centimeter beyond the outer boundary of the respective electrodes 510-1 and 510-2.

In some embodiments, wiring between a microchip and electrodes is used to create a pattern within a film section of a patch including a device. In an embodiment, the pattern is a trace pattern. An example wire diagram illustrating such a trace pattern is now described with respect to FIG. 6. In some embodiments, the wire traces are embedded in the thin film.

Figure 6:
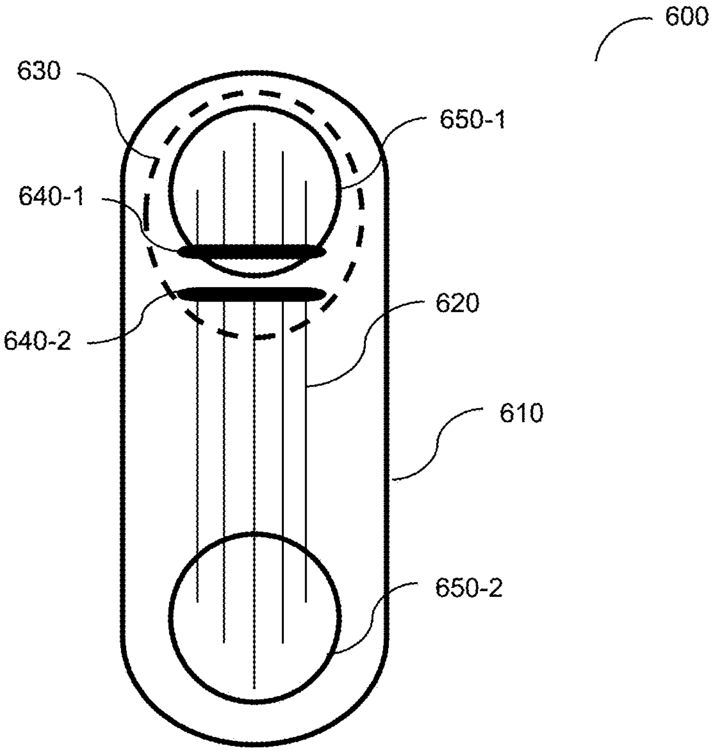
FIG. 6 is a wire diagram illustrating connections between terminals and electrodes according to an embodiment.

FIG. 6 is a wire diagram 600 illustrating connections between terminals and electrodes according to an embodiment. As depicted in FIG. 6, a device 610 has a set of wires 620 forming a trace pattern. The wire diagram 600 further indicates a location 630 upon which a housing (not shown) may be placed. Such a housing may include, but is not limited to, a circuit board and a battery. Non-limiting example housing components are described further below with respect to FIG. 14. In some embodiments, a microphone (not shown) may also be included.

The wire diagram 600 further illustrates a set of connection terminals 640-1 and 640-2 which may be utilized to electrically connect to a microchip disposed in the housing (not shown) placed upon the location 630. Such a microchip may have two separate outputs which may connect to two distinct respective electrodes 650-1 and 650-2. In some embodiments, a plurality of distinct outputs and electrode contacts points can be used. Multiple electrodes allow for current to flow inwards from one electrode into the tissue and outwards from the tissue into the other electrode. In a further embodiment, one of the electrodes (e.g., the electrode 650-1) only connects to one terminal (e.g., the terminal 640-1), while the other electrode (e.g., the electrode 650-2) only connects to another terminal (e.g., the terminal 640-2).

Figure 7:
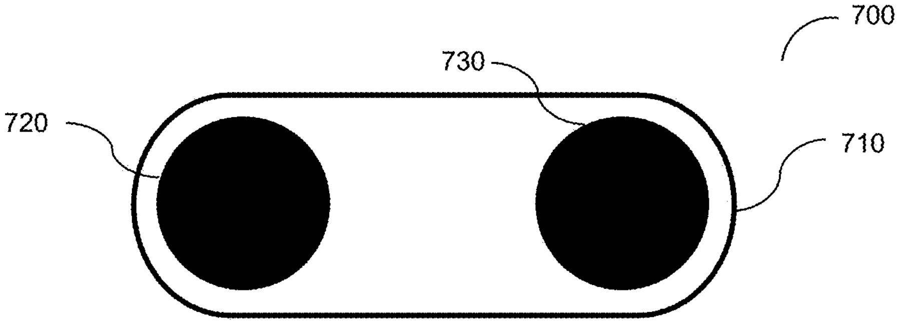
FIG. 7 is a diagram illustrating a bandage-shaped design of a device according to an embodiment.

FIG. 7 is a diagram illustrating a bandage-shaped design of a patch 700 according to an embodiment. As depicted in FIG. 7, the patch 700 includes a surface 710 with two electrodes 720 and 730 disposed thereon. The surface 710 may be made of one or more layers such as, but not limited to, an adhesive layer. In some embodiments, the adhesive layer is located on the entire surface 710 of the patch 700 except for portions of the surface 710 where the electrodes 720 and 730 are disposed. In some embodiments, the edges of the patch 700 are rounded in order to improve comfort at skin interface. An example set of layers which may be utilized to realize the surface 710 is discussed further below with respect to FIG. 11.

It should be noted that the various embodiments discussed with respect to FIGS. 3-7 are described with respect to two electrodes, but that additional electrodes may be utilized in accordance with at least some disclosed embodiments. Moreover, the electrodes depicted in FIGS. 3-7 are circular in shape, but that other shapes may be equally utilized without departing from the scope of the disclosure.

Figure 8:
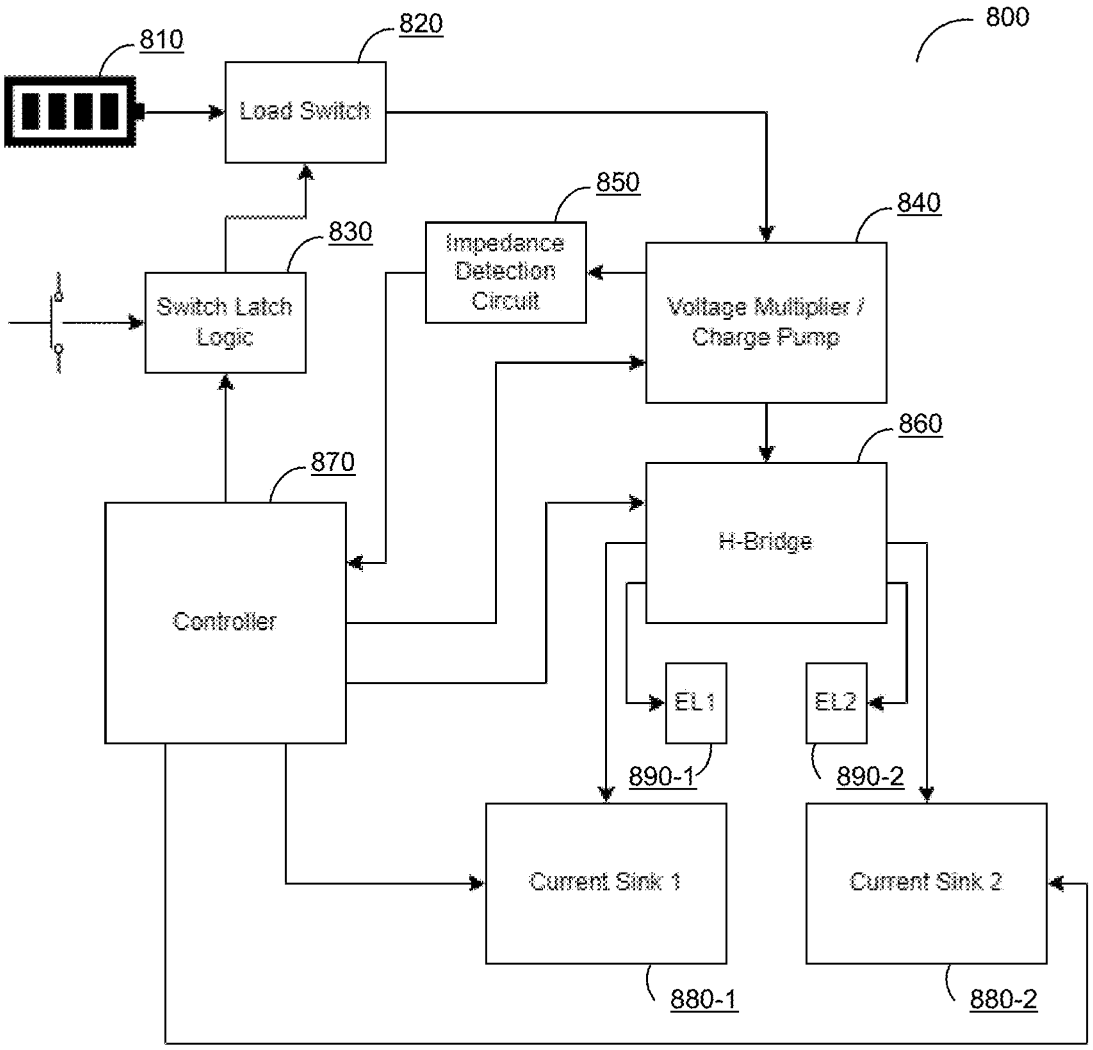
FIG. 8 is a schematic diagram of electrical components in accordance with various disclosed embodiments.

FIG. 8 is a schematic diagram 800 of electrical components in accordance with various disclosed embodiments. The diagram 800 illustrates an example system topology.

The example system topology illustrated in FIG. 8 may be realized on or otherwise via a printed circuit board (PCB, not shown in FIG. 8). In some non-limiting implementations, the PCB may be a rigid type PCB. In other implementations, a flex type PCB may be utilized.

As depicted in FIG. 8, an electrical source 810 such as a battery is electrically connected to a load switch 820, which in turn is communicatively connected to switch latch logic 830 and to a voltage multiplier 840. The voltage multiplier 840 may be, but is not limited to, a Dickson charge pump, and may be utilized for a current sink supply. The voltage multiplier 840 is connected to an impedance detection circuit 850 and a H-bridge 860.

In at least some implementations, the electrical source 810 is adapted such that it is capable of powering a device as described herein for at least 8 hours of continuous use. In a further implementation, the electrical source 810 is adapted to enable at least 12 hours of continuous device use. The electrical source 810 may be, but is not limited to, a non-rechargeable battery, a durable rechargeable battery, and the like. Non-limiting example types of battery which may be utilized in accordance with various implementations include alkaline, lithium-ion, lead-acid, nickel-cadmium, nickel-metal hydride, lithium polymer, zinc-Carbone, silver oxide, zinc-air, and the like.

In an embodiment, the electrical source 810 is adapted such that a device including the electrical source 810 is adapted to apply a continuous stimulation pattern for a time period between 1 and 12 hours. In a further embodiment, the device is adapted such that a maximum length of time of quiescence is 10 seconds during the time period in which the continuous stimulation pattern is applied. That is, the maximum duration of any period of inactive time (i.e., time in which pulses are not being emitted) during the stimulation is 10 seconds. In another embodiment, the device is adapted such that a maximum length of time of quiescence is 100 milliseconds during the time period in which the continuous stimulation pattern is applied.

Outputs of the impedance detection circuit 850 are input to a controller 870, which in turn sends control signals to the switch latch logic 830, the voltage multiplier 840, the H-bridge 860, a first current sink 880-1, and a second current sink 880-2. An additional charge pump (not shown) may be integrated into a chip (not shown) of the controller 870 in order to provide a target voltage output such as, but not limited to, an output of about 9 volts with a maximum current amplitude of around 10 milliamps. The H-bridge 860 may deliver power to a pair of electrodes 890-1 and 890-2.

In an embodiment, the system topology shown in FIG. 8 is utilized to deliver an output current pulse having an amplitude between 4 and 12 Milliamps (mA), a square bi-polar (biphasic) waveform, having two phases each with a width of 100 microseconds per phase (for a 200 microsecond long total pulse), and a repetition frequency of 30 Hertz (Hz). In some embodiments, the frequency is between 15 and 90 Hz. In some embodiments, the width per phase is between 50 and 500 microseconds. In some embodiments, the phases have different widths.

That is, the system topology may be utilized to repeatedly deliver stimulation pulses. These pulses have an induced change in electrical potential between two points (e.g., points of electrodes as discussed herein), which causes current to flow through the tissue between the electrodes 890-1 and 890-2. In some embodiments, the pulses are biphasic pulses which alternate the current direction at some point during the pulse (which prevents charge build up in the tissue and improves activation of neural targets). In a further embodiment, the amplitude may be configurable to different predetermined settings. In yet a further embodiment, the predetermined settings include 5 mA, 7 mA, and 9 mA. In another embodiment, the current pulse which is delivered is between 7 to 12 mA. Alternatively, the current pulse which is delivered is less than or equal to 60 mA. It has been discovered that 60 mA is likely a top end of a safe range of potential amplitude values. It has also been identified that 7 to 12 mA may provide optimal stimulation conditions for at least some disclosed embodiments. It has been identified that such ranges tend to be comfortably tolerated by subjects with normal body mass index. Higher current levels (up to 60 mA) may be used in at least some embodiments in order to properly reach and engage the vagus nerve in targets with relatively more deep vagus nerve locations relative to skin surface (e.g., obese users).

In some embodiments, a time of around 0.01 milliseconds (ms) is inserted between phases of the biphasic pulse in order to produce an interphase gap. In this regard, it has been identified that such an interphase gap has demonstrated effectiveness in improving activation of target neural structures, which in turn can further enhance sensory processing, minimize or avoid side effects of nerve stimulation, or both, in accordance with various disclosed embodiments.

In another embodiment, an asymmetric biphasic waveform is used. More specifically, in a further embodiment, a second phase of the biphasic waveform is between 10 and 30 percent weaker than a first phase (e.g., weaker as measured in current amps, i.e., 10 to 30 percent lower current amps). In this regard, it is identified that symmetric biphasic waves can, in at least some instances, cause depolarization from charge build up over time because the potential within the tissue is affected slightly differently by the first and second phase due to the effects of the first phase slightly influencing the effects of the second phase (e.g., during extended use). Accordingly, using a slightly asymmetric biphasic waveform such as a waveform where the second phase is 10 to 30 percent weaker than the first phase may avoid or otherwise mitigate depolarization.

In some embodiments, electrical current is provided according to a ramp-up procedure. In such a ramp-up procedure, the full amplitude current of the stimulation pattern to be applied is not provided initially when the device or patch is applied to the skin. In this regard, it has been identified that a sudden change from no stimulation to full strength stimulation (e.g., at a rate of over 10 mA/second) may be shocking or uncomfortable for the user. To this end, in some further embodiments, amplitude may be increased in incremental steps (e.g., increasing by 0.05 mA/second). In a further embodiment, a ramp-up pace between 1 and 10 mA/second is utilized to increase the amplitude in incremental steps. In yet a further embodiment, a ramp-up pace between 1 and 5 mA/second is utilized. In this regard, it has been discovered that a ramp-up pace between 1 and 5 mA/second tends to provide the least amount of discomfort.

In a further embodiment, the ramp-up procedure begins with an immediate increase in stimulation to a first level, and then incrementally increasing the amplitude to a second level (i.e., the full amplitude current to be delivered) in multiple increments. In some embodiments, a current value between 1 and 5 mA is used as the first level to be applied immediately upon stimulation beginning. In a further embodiment, a current value of 5 mA is used as the first level, and a current value between 7 and 12 mA is used as the second level (full amplitude current). Alternatively, the second level may be any value up to 60 mA.

In this regard, it has been discovered that a slow ramp-up to the full amplitude current tends to cause more discomfort for users than an immediate jump to a lower level of current followed by a ramp-up to the full level of current. It has further been discovered that current values between 1 and 5 mA are the lowest perceptible current for most individuals using the stimulation pattern as described herein. It has also been identified that some individuals exhibit more discomfort for current values between 1 and 5 mA than for a current value of 5 mA such that, for some implementations, it may be desirable to jump immediately to 5 mA to minimize discomfort. It has further been discovered that maximum current values between 7 and 12 mA have been found to provide adequate stimulation for many use cases without causing significant levels of discomfort such that current values between 7 and 12 mA may be suitable full amplitude current values. That said, it has been discovered that current values up to 60 mA are safe levels even if some higher current values up to 60 mA may cause additional discomfort. In that regard, it is noted that some implementations and use cases may tolerate additional discomfort in exchange for a higher current (e.g., to further enhance sensory processing). For example, a military use case, a life-or-death situation, or an athlete may tolerate some degree of discomfort for further improved performance.

In an embodiment, the frequency, waveform, or both, of the stimulation pattern may affect the thresholds to be used. For example, certain frequencies or waveforms may be perceptible at current values outside of 1 to 5 mA and, consequently, the first level may be set to a different current value in accordance with certain embodiments and implementations in order to cause initial perception while reducing overall discomfort.

In order to provide a ramp-up as discussed above and to ensure that current is only delivered when product is properly applied to skin, in some embodiments, a circuit designed to deliver transcutaneous stimulation is adapted to measure an impedance value of an attached load and to deliver stimulation when an appropriate load is indicated (e.g., above a predetermined threshold or within a predetermined range of appropriate loads such as, but not limited to, between 500 and 2000 ohms). The ramp-up may be facilitated by adjusting, for example but not limited to, a time course of a charging capacitor which is adapted to create a voltage signal that ramps up over time until it reaches a saturation value and for which the ramp rate properties can be adjusted by varying properties of the capacitor.

Figure 9:
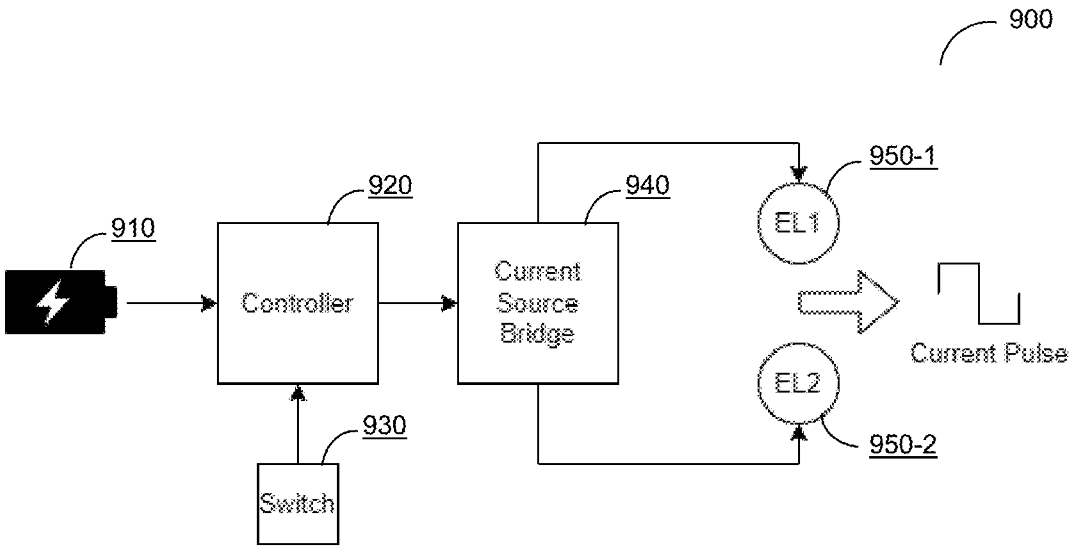
FIG. 9 is a system diagram utilized to describe various disclosed embodiments.

FIG. 9 is a system diagram 900 utilized to describe various disclosed embodiments. As depicted in FIG. 9, a power source 910 provides power to a controller 920. The controller 920 is activated via a switch 930. The controller 920 sends control signals to a current source bridge 940, which in turn power a pair of electrodes 950-1 and 950-2.

The controller 920 may be realized via one or more chips such as, but not limited to, microchips. As discussed herein, such microchips may be disposed on a printed circuit board (PCB) and enclosed in a housing. The housing may further be designed to create a tight seal in order to prevent water or other fluids from entering the housing and affecting the controller 920. In some embodiments, the chip is enclosed within a film of a patch (not shown) without requiring a housing.

In some embodiments, a physical switch 930 is adapted to keep a battery such as the power source 910 electrically disconnected from the electrodes 950-1 and 950-2 until the battery is removed from packaging (not shown). This may be utilized in order to prevent the battery from draining while in transit and storage. In some embodiments, a digital switch 930 may further be connected to one or more sensors (not shown) configured to measure one or more metrics such as, but not limited to, impedance, current, voltage, resistance, combinations thereof, and the like. Measuring these metrics allows for determining whether any of these metrics are above a threshold, below a threshold, between thresholds, and the like. In such an embodiment where the switch 930 is connected to sensors, the switch 930 is configured to turn on or off depending on whether one or more metrics are above, below, or between, respective thresholds. In this regard, a device incorporating the switch 930 and any such sensors is adapted to monitor metrics such as impedance, current, voltage, or resistance, and to turn on (thereby applying current) or shut down (thereby ceasing application of current). Sensors or other components used to measure such metrics may include, but are not limited to, voltage dividers, a resistor with a known value resistance or impedance, one or more comparator circuits (e.g., circuits configured to compare voltage with a reference voltage in order to output values indicating when one voltage is higher than the other), digital control logic, combinations thereof, and the like.

In particular, in some embodiments, a resistive sensor adapted to measure resistance is connected to the switch 930, and the switch 930 is configured to turn on when the resistance measured by the resistive sensor is above a predetermined threshold. Turning the device on when a certain amount of resistance has been detected may be utilized to effectively determine whether a patch or device as described herein is applied to skin and delivering current as described herein only when the device is applied to skin.

In another embodiment, an impedance sensor adapted to measure impedance across the electrodes 950-1 and 950-2 is connected to the switch 930, and the switch 930 is configured to turn on when the impedance measured by the impedance sensor is above a threshold, below a threshold, or within a range bound by thresholds. In this regard, a device incorporating the switch 930 and such an impedance sensor may be effectively adapted to shut down when an appropriate load is not present as defined with respect to one or more predetermined thresholds (e.g., when the impedance is below a predetermined threshold, above a predetermined threshold, outside of a range, combinations thereof, etc.). In a further embodiment, the range of appropriate loads may be between 400 and 4000 Ohms. In some embodiments, stimulation may resume when the load is once again at an appropriate level (e.g., above a threshold, below a threshold, or within a range).

In this regard, it is noted that a device not being appropriately applied to skin may cause impedance or other metrics to fall outside of safe ranges. In such a case, for example, when electrodes of a device are placed such that they do not fully contact an appropriate surface area of the user's skin, such a lack of full contact may cause any current delivered to the skin to exceed a safe or comfortable amount of current given the surface area to which the current is effectively applied. As a non-limiting example, when the device is implemented in a patch which begins to peel such that one of the electrodes ceases being in contact with the skin, a situation in which the device would send the same amount of current through half of the normal surface area of the skin may occur. This imbalance of current to surface area may cause discomfort or injury such that detecting impedance above a threshold and ceasing stimulation when impedance is above the threshold may avoid discomfort or injury. To this end, in an embodiment, the device may be adapted to cease stimulation when the impedance is above a threshold of 10,000 ohms.

Likewise, impedance below a threshold may indicate that the device has short circuited such that the electrodes are not properly electrically isolated from each other. For example, in an embodiment, a normal impedance range may be between 200 and 4000 ohms such that an impedance below 200 ohms may be indicative of a short circuit. In such a case, the device may shut off when the impedance drops below 200 ohms. Impedance may be measured using components or techniques such as, but not limited to, time-domain reflectometry, frequency domain analysis, Wheatstone bridge, impedance-to-digital conversion chips, combinations thereof, and the like.

Similarly, other safety or proper operation thresholds may include, but are not limited to, overvoltage protection thresholds (e.g., over 24 volts), undervoltage protection thresholds (e.g., less than 1 volt), overcurrent protection thresholds (e.g., greater than 1 milliamp above target current), combinations thereof, and the like.

In some embodiments, the switch 930 may be physically attached to packaging such that the switch 930 is pulled (and therefore activated) as part of removing the device from the packaging. In such an implementation, the switch 930 may be realized as a pull-tab or tear strip switch. In other implementations, the switch 930 may be magnetic and held in an "off" position by a small magnet included in the packaging for the device. When the packaging is removed from the device, the removal of the magnet causes the switch 930 to change to an "on" position. Other types of switches (e.g., optical, capacitive, inductive, etc.) may be utilized without departing from the scope of the disclosure.

In other embodiments, the switch 930 may be connected to a button (not shown) disposed on a device such that, when the button is pressed, the switch 930 may activate stimulation as discussed herein. The button may be realized as, for example but not limited to, a toggle, rocker, push, slide, tactile button, capacitive button, physical switch, combination thereof, and the like. In a further embodiment, pressing the button while current is being delivered (i.e., while stimulation is active) may cause the stimulation to deactivate and current to cease being delivered. Some such embodiments may utilize multiple switches or otherwise allow for both activating/deactivating the device via press of a button and activating or deactivating the device when one or more electrical metrics (e.g., voltage, current, impedance, resistance, etc.) meet a threshold or fall within a range as discussed above.

Figure 10:
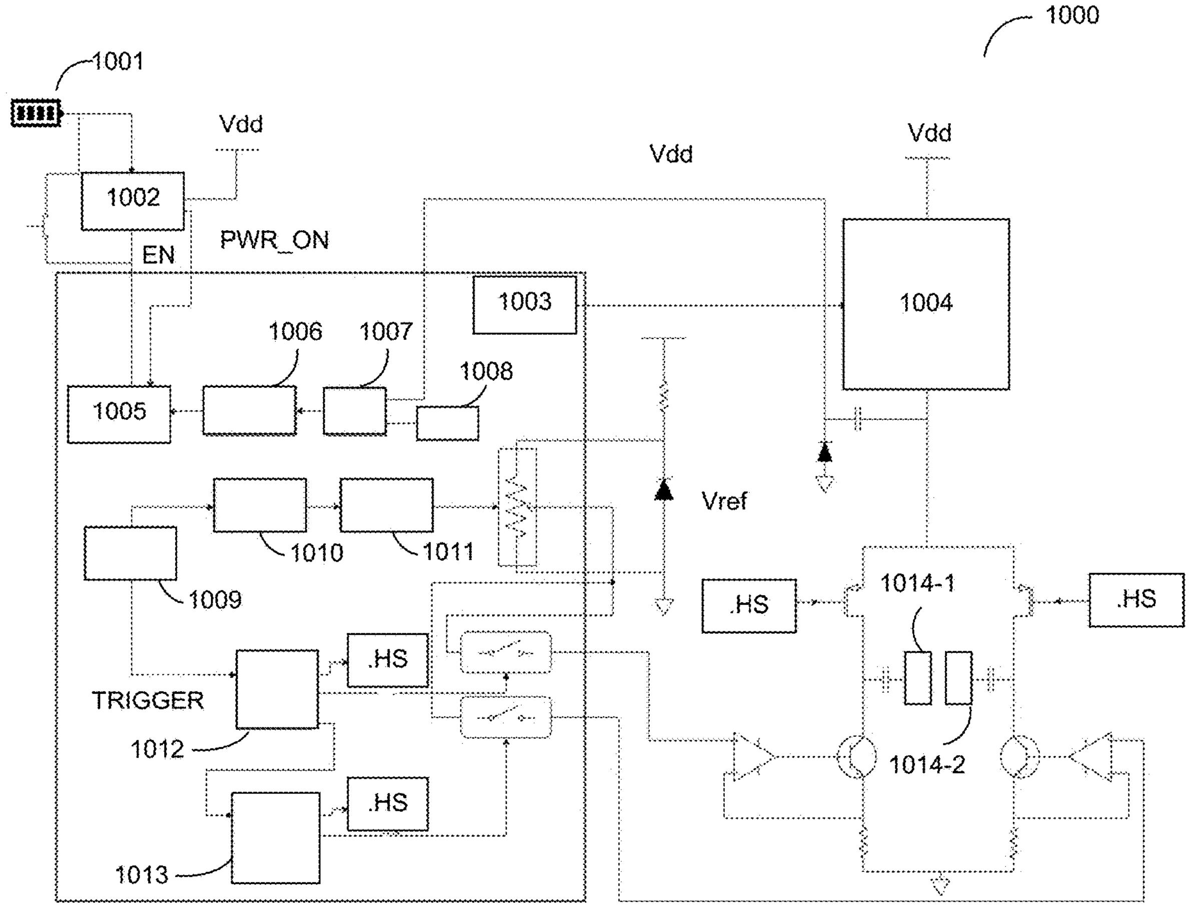
FIG. 10 is a hardware architecture diagram utilized to describe various disclosed embodiments.

FIG. 10 is a hardware architecture diagram 1000 utilized to describe various disclosed embodiments. The hardware architecture diagram illustrates connections and flows between components including a power source 1001, a load switch 1002, a first clock (e.g., a 1 Kilohertz CLK) 1003, a voltage multiplier or charge pump 1004, a circuit (e.g., a S-R latch 1005), a watch-dog logic component 1006, a comparator 1007, a threshold 1008, a second clock (e.g., a 30 Hertz CLK) 1009, a third clock (e.g., a 1 Hertz CLK) 1010, a ramp logic component 1011, a first pulse generator (e.g., a 100 microsecond pulse generator) 1012, a second pulse generator (e.g., a 100 microsecond pulse generator) 1013, and a pair of electrodes 1014-1 and 1014-2. The ramp logic component 1011 is designed to control ramping up of current, for example as discussed further above.

Figure 11:
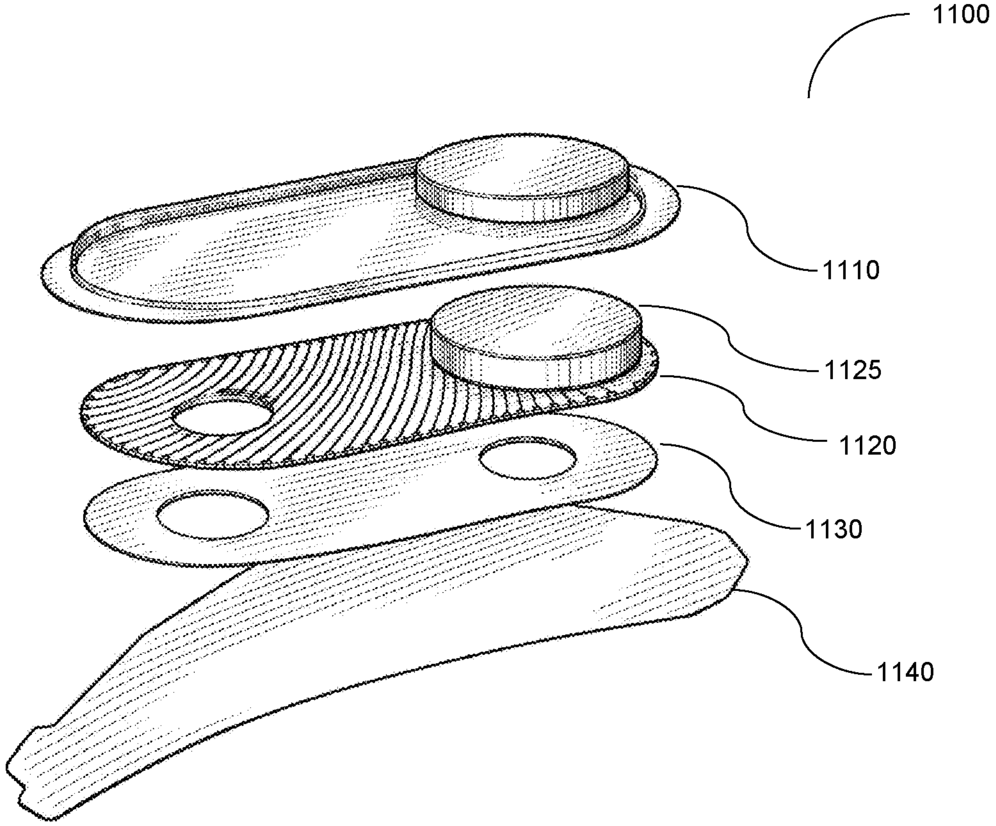
FIG. 11 is a top exploded view illustrating components of a device according to an embodiment.

FIG. 11 is a top exploded view illustrating components of a patch 1100 according to an embodiment. The top exploded view illustrates components including a top cover 1110, a housing 1125 disposed on an electrode apparatus 1120, an adhesive layer of the adhesive layer 1130 of the patch 1100, and a bottom layer 1140. Specifically, FIG. 11 illustrates an assembled version of the patch 1100 including packaging components in the form of a top cover 1110 and a bottom layer 1140.

The top cover 1110 depicted in FIG. 11 is made of a plastic material which may be utilized to protect the patch 1100, for example, during shipping. As discussed above, in some implementations, a film (not shown) may be utilized as a top layer instead of the top cover 1110 depicted in FIG. 11.

The housing 1125 is disposed on the electrode apparatus 1120 and may house components such as, but not limited to, electrodes, wires, circuit boards, and the like. Example components which may be housed in the housing 1125 are described further below with respect to FIG. 14.

The adhesive layer 1130 may be glue or another adhesive used to secure the electrode apparatus 1120 to the skin of the user. The top cover 1110, in order to seal the electrode apparatus 1120 and housing 1125 within a sealed chamber, creates a chamber formed between the top cover 1110 and the bottom layer 1140.

That is, the top cover 1110 and the bottom layer 1140 may be affixed in order to form a chamber holding the components of the patch 1100 during shipping. To this end, the bottom layer 1140 may further include one or more adhesives (not shown) which are used to adhere the bottom layer 1140 to the top cover 1110. The top cover 1110 and the bottom layer 1140 may be separated in order to remove the patch 1100 from such a chamber such that remaining components (e.g., the electrode apparatus 1120 and the adhesive layer 1130) may be removed from the packaging when the electrode apparatus 1120 is to be applied to the skin of a user.

The adhesive layer 1130 covers a surface of the patch 1100 where the patch 1100 is to be attached to the skin of a user and may further be utilized to create an electrically insulating barrier between electrodes. Such an electrically insulating barrier may prevent liquids or other foreign materials from creating a short circuit. In some embodiments, the adhesive layer 1130 is made out of silicone, acrylic, hydrocolloid, polyurethane, Tegaderm, and the like.

In some embodiments, an area of a portion of the adhesive surrounding each electrode of the electrode apparatus 1120 is around 0.5 centimeters thick. Such a 0.5 centimeter thick area around the portion of the adhesive may allow for holding the electrodes to the skin and creating a waterproof seal around the electrodes. In a further embodiment, a thickness of the adhesive is at least 5 millimeters in order to provide a waterproof barrier, a conduction barrier, or both.

In some embodiments, the adhesive layer 1130 may be further attached to a backing layer (not shown) that covers the adhesive until the patch 1100 is to be used. Such a backing layer may have a thickness of around 0.1 millimeters.

In some embodiments, the adhesive layer 1130 of the patch 1100 that interfaces with the skin may be made of two materials including an adhesive material and a conductive material (not shown), where the sections of the conductive material may act as electrodes to deliver electrical current in accordance with one or more disclosed embodiments. In such embodiments, the portion of the adhesive layer 1140 made of the adhesive material is between 0.1 and 1 millimeters thick.

Figure 12:
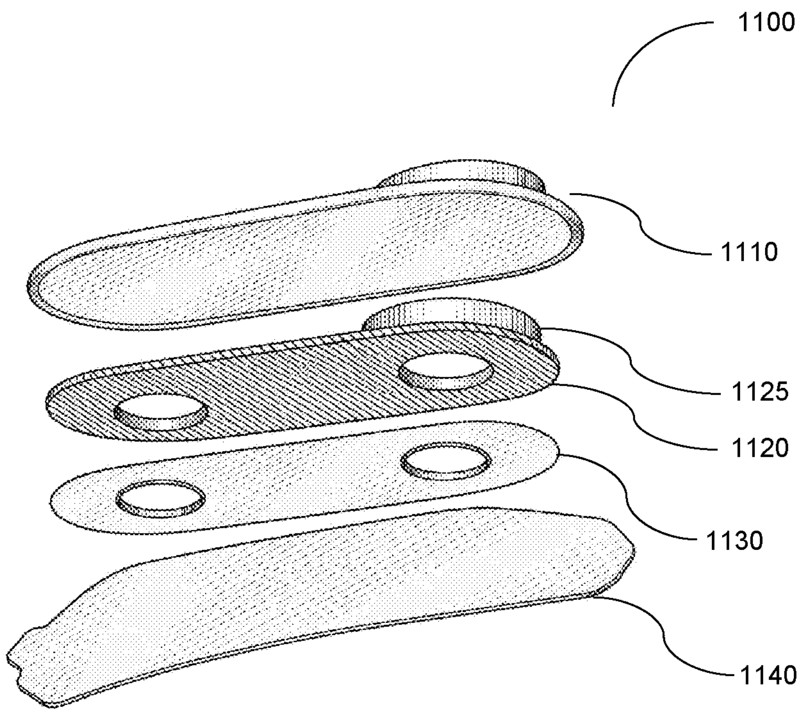
FIG. 12 is a bottom exploded view illustrating components of a device according to an embodiment.

FIG. 12 is a bottom exploded view illustrating the components of the patch 1100 according to an embodiment.

Figure 13:
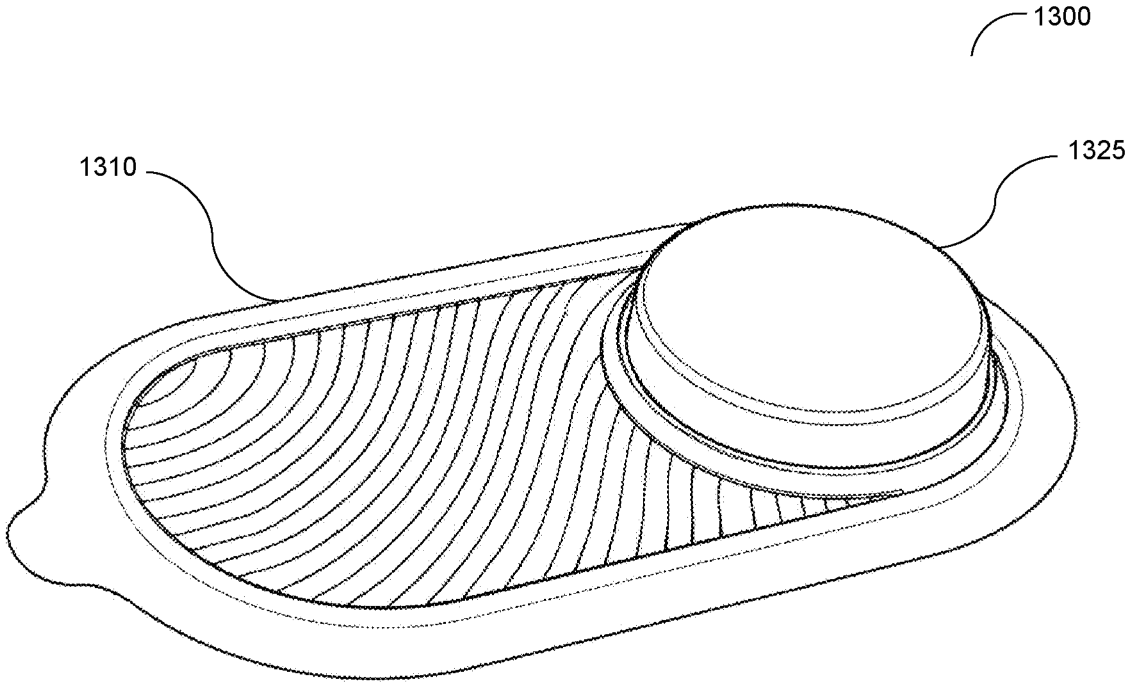
FIG. 13 is an assembled view of a device according to an embodiment.

FIG. 13 is an assembled view 1300 of a device according to an embodiment. The assembled view 1300 illustrates a top cover 1310 and a housing 1325. The housing 1325 may include components as now described with respect to FIG. 14.

Figure 14:
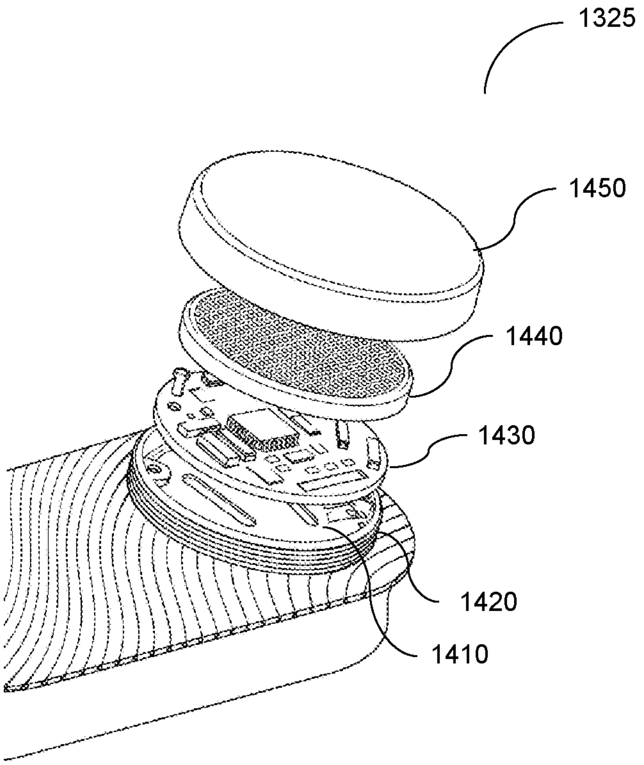
FIG. 14 is an exploded view of a housing according to an embodiment.

FIG. 14 is an exploded view of the housing 1325 according to an embodiment. The housing 1325 includes a connecting member 1410, a base 1420, a circuit board 1430, a battery 1440, and a cover 1450. The connecting member 1410 may be disposed on or attached to a device (e.g., the patch 700, FIG. 7), and may facilitate electrically connecting the circuit board 1430 with an electrode (e.g., the electrode 720 or the electrode 730, FIG. 7), for example via one or more wires as discussed above with respect to FIG. 6.

The base 1420 may be affixed to the cover 1450 in order to enclose the housing between the device and the connecting member 1410 with the cover 1450. The base 1420 and the cover 1450 may therefore be utilized to realize an enclosed cavity in which the other components of the device shown in FIG. 14 are disposed.

The circuit board 1430 may be configured to deliver electric pulses when the device is disposed on a nerve as described herein. To this end, the circuit board 1430 is electrically connected to the battery 1440. The battery 1440 provides electricity for distribution to electrodes (e.g., the electrodes 720 and 730 as shown in FIG. 7).

Figure 15:
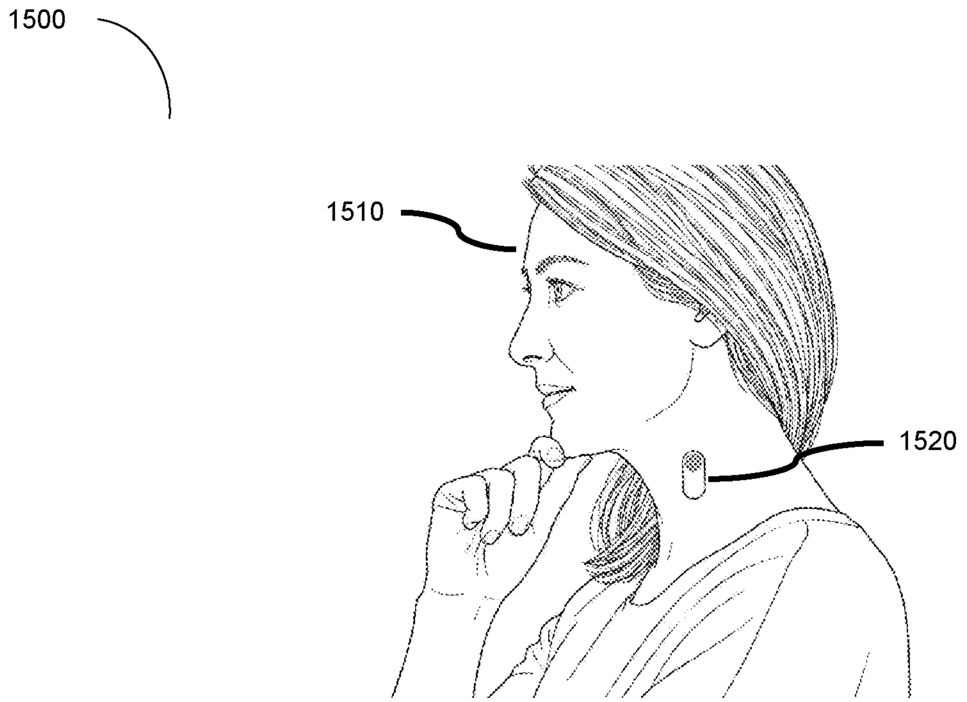
FIG. 15 is an illustration of a device placed on a user.

FIG. 15 is an illustration 1500 of a patch 1520 placed on a user 1510. The patch 1520 may be designed in accordance with one or more of the disclosed embodiments, for example, as described above with respect to FIGS. 11-14.

Figure 16:
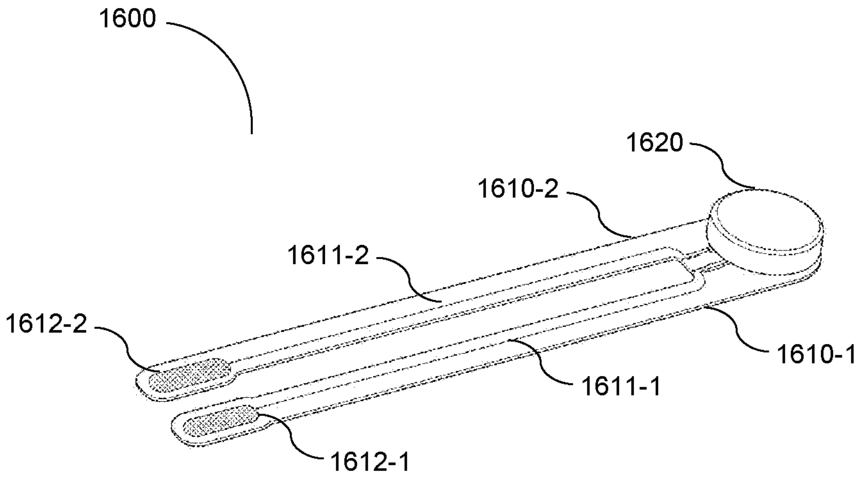
FIG. 16 is a diagram illustrating a dual-member design of a device according to an embodiment.

FIG. 16 is a diagram illustrating a dual-member design of a device 1600 according to an embodiment. The device 1600 depicted in FIG. 16 shows a housing of a device (e.g., housing enclosing components such as those described further above with respect to FIG. 14) and a pair of elongated members 1610-1 and 1610-2. As depicted in FIG. 16, the members 1610-1 and 1610-2 includes wire leads 1611-1 and 1611-2, respectively, and electrodes 1612-1 and 1612-2, respectively.

In an embodiment, a length of each of the members 1610-1 and 1610-2 is around half of a predetermined neck circumference value (e.g., a known average neck circumference). In a further embodiment, the length of each of the members 1610-1 and 1610-2 is between 5 and 10 inches.

In an embodiment, the wire leads 1611-1 and 1611-2 are the same or roughly the same distance. The members 1610-1 and 1610-2 may be spaced such that the electrodes 1612-1 and 1612-2 are located at least a threshold distance apart (e.g., between 2 and 6 centimeters) such that the electrodes 1612-1 and 1612-2 may be placed such a threshold distance apart on the carotid triangle in order to enable stimulation as discussed herein. For example, a distance between center lines of the members may be equal to or otherwise based on an interelectrode distance of the electrodes. In a further embodiment, the electrodes 1612-1 and 1612-2 are around 3 to 4 centimeters apart as measured from center point to center point. Moreover, as discussed above, in at least some embodiments, the surface area of each of the electrodes 1612-1 and 1612-2 may be at least 2 square centimeters in order to maintain a total ratio of electrode to skin surface area for ensuring current density during stimulation without increasing current density to a level where discomfort or injury might occur.

The device 1600 may further include a housing 1620 containing components such as, but not limited to, a power source (e.g., a battery) and a controller (e.g., a microchip).

Figure 17:
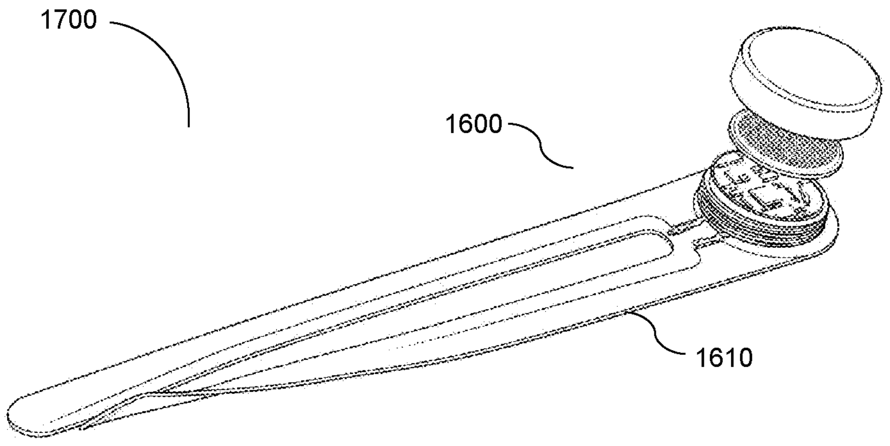
FIG. 17 is a diagram illustrating flexibility of members of a device according to an embodiment.

FIG. 17 is a diagram 1700 illustrating flexibility of members of the device 1600 according to an embodiment. As depicted in FIG. 17, the device 1600 includes members 1610 which are flexible. Such flexibility may allow the members 1610 to be adjusted to the contours of a user's neck in order to improve comfort, appearance, both, and the like.

In some embodiments, the members 1610 of the device 1600 may include angled ends in order to facilitate a desired spacing of the electrodes. An example of such angled members is now described with respect to FIG. 18.

Figure 18:
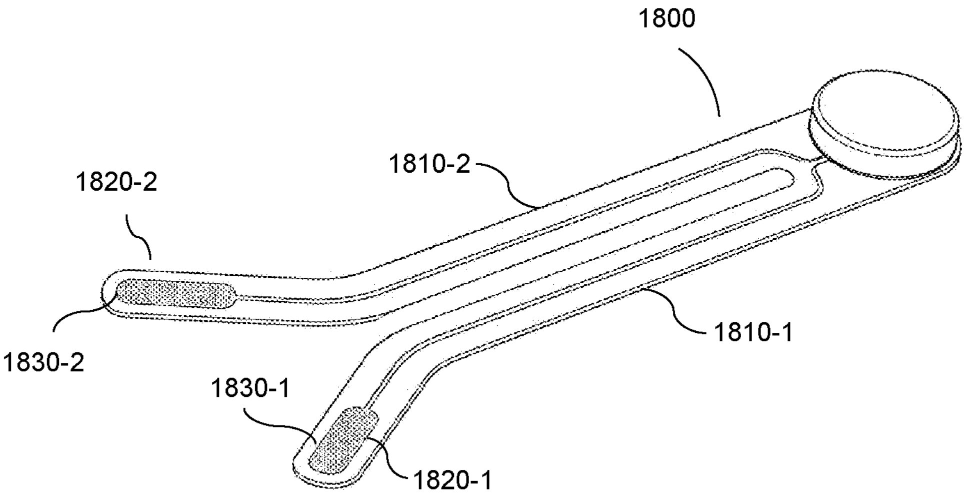
FIG. 18 is a diagram illustrating a forked dual-member design of a device according to an embodiment.

FIG. 18 is a diagram illustrating a forked dual-member design of a device 1800 according to an embodiment. As depicted in FIG. 18, the device 1800 includes a pair of members 1810-1 and 1810-2. The members 1810-1 and 1810-2 have forked ends 1820-1 and 1820-2 having electrodes 1830-1 and 1830-2, respectively. The forked design of the device 1800 may further aid a user in properly placing the device 1800 for stimulation and, in particular, to ensure appropriate spacing of the electrodes 1830-1 and 1830-2. To this end, in some embodiments, the forked ends 1820-1 and 1820-2 diverge from a direction of their respective members 1810-1 and 1810-2 at an angle between 30 and 60 degrees. In a further embodiment, the forked ends 1820-1 and 1820-2 diverge at a point that is between 1 to 2 inches from the electrodes 1830-1 and 1830-2 (e.g., as measured from center points of the electrodes 1830-1 and 1830-2) in order to ensure that the center points of the electrodes 1830-1 and 1830-2 are appropriately spaced.

Figure 19:
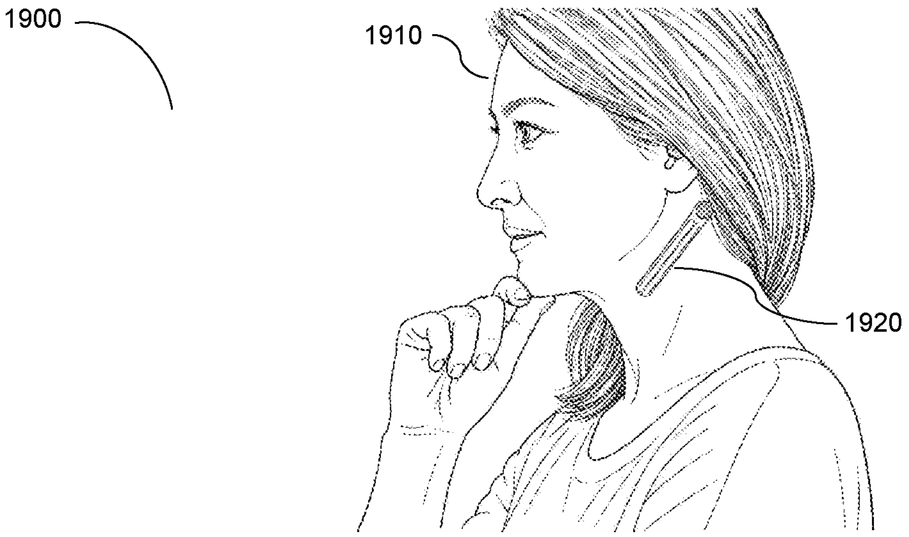
FIG. 19 is an illustration of a dual-member device placed on a user.

FIG. 19 is an illustration 1900 of a dual-member device 1920 placed on a user 1910. As depicted in FIG. 19, the device 1920 may be placed such that the members are disposed on a carotid triangle of the user 1910 and a housing may be placed higher up on the user's neck, which may allow the housing to be partially or fully hidden from view, for example for aesthetic purposes.

Figure 20:
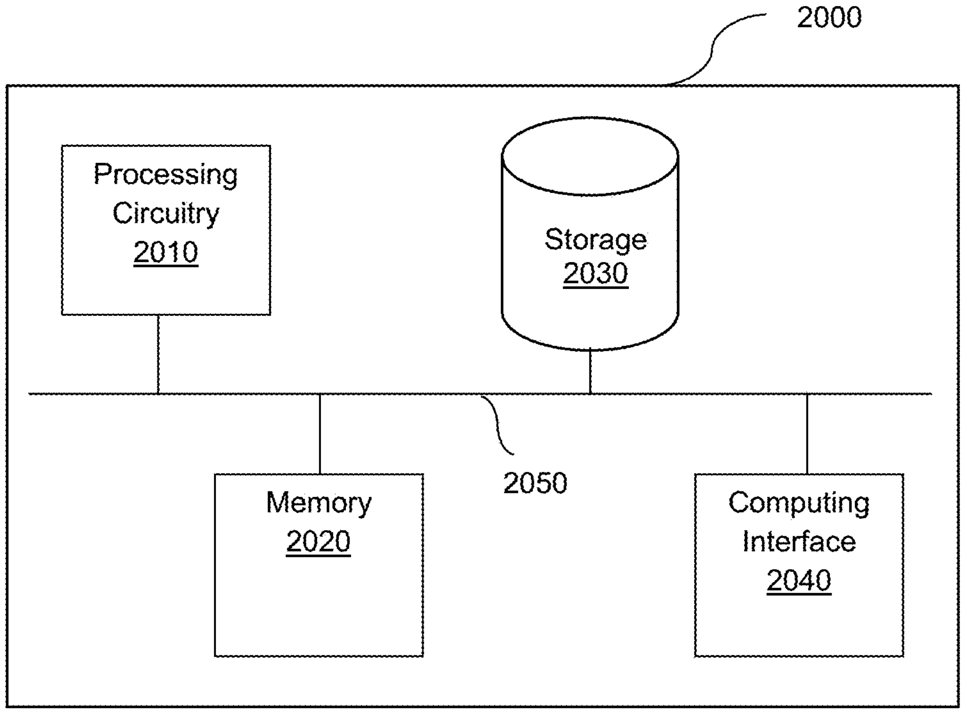
FIG. 20 is a schematic diagram of a hardware layer of computing components of a device according to an embodiment.

FIG. 20 is a schematic diagram of a hardware layer 2000 of computing components of a device according to an embodiment. The hardware layer 2000 includes a processing circuitry 2010 coupled to a memory 2020, a storage 2030, and a computing interface 2040. In an embodiment, the components of the hardware layer 2000 may be communicatively connected via a bus 2050.

The processing circuitry 2010 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 2020 may be volatile (e.g., random access memory, etc.), non-volatile (e.g., read only memory, flash memory, etc.), or a combination thereof.

In one configuration, software for implementing one or more embodiments disclosed herein may be stored in the storage 2030. In another configuration, the memory 2020 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 2010, cause the processing circuitry 2010 to perform the various processes described herein.

The storage 2030 may be magnetic storage, optical storage, and the like, and may be realized, for example, as flash memory or other memory technology, compact disk-read only memory (CD-ROM), Digital Versatile Disks (DVDs), or any other medium which can be used to store the desired information.

The computing interface 2040 allows the hardware layer 2000 to communicate with other systems, devices, components, applications, or other hardware or software components, for example as described herein. In some implementations, the computing interface 2040 may be or may include a network interface, for example, a network interface used to communicate with one or more user devices having installed thereon software for delivering audio content to a user as discussed below with respect to FIG. 23.

It should be understood that the embodiments described herein are not limited to the specific architecture illustrated in FIG. 20, and other architectures may be equally used without departing from the scope of the disclosed embodiments.

Figure 21:
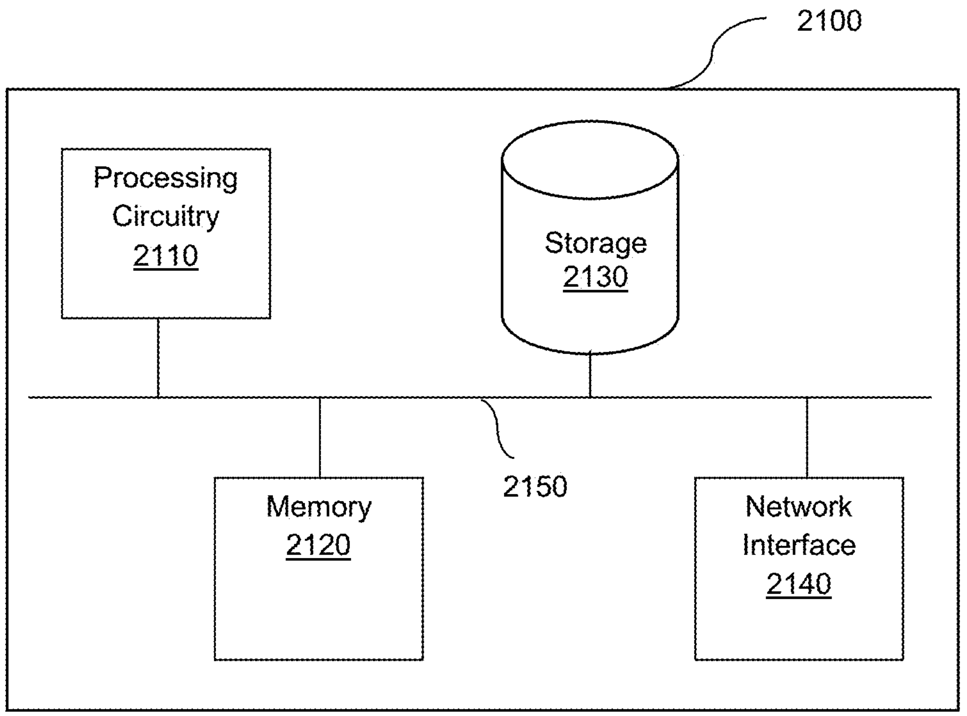
FIG. 21 is a schematic diagram of a user device according to an embodiment.

FIG. 21 is a schematic diagram of a user device 2100 according to an embodiment. The user device 2100 includes a processing circuitry 2110 coupled to a memory 2120, a storage 2130, and a computing interface 2140. In an embodiment, the components of the user device 2100 may be communicatively connected via a bus 2150.

The processing circuitry 2110 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 2120 may be volatile (e.g., random access memory, etc.), non-volatile (e.g., read only memory, flash memory, etc.), or a combination thereof.

In one configuration, software for implementing one or more embodiments disclosed herein may be stored in the storage 2130. In another configuration, the memory 2120 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 2110, cause the processing circuitry 2110 to perform the various processes described herein.

The storage 2130 may be magnetic storage, optical storage, and the like, and may be realized, for example, as flash memory or other memory technology, compact disk-read only memory (CD-ROM), Digital Versatile Disks (DVDs), or any other medium which can be used to store the desired information.

The computing interface 2140 allows the user device 2100 to communicate with other systems, devices, components, applications, or other hardware or software components, for example as described herein.

It should be understood that the embodiments described herein are not limited to the specific architecture illustrated in FIG. 21, and other architectures may be equally used without departing from the scope of the disclosed embodiments.

Figure 22:
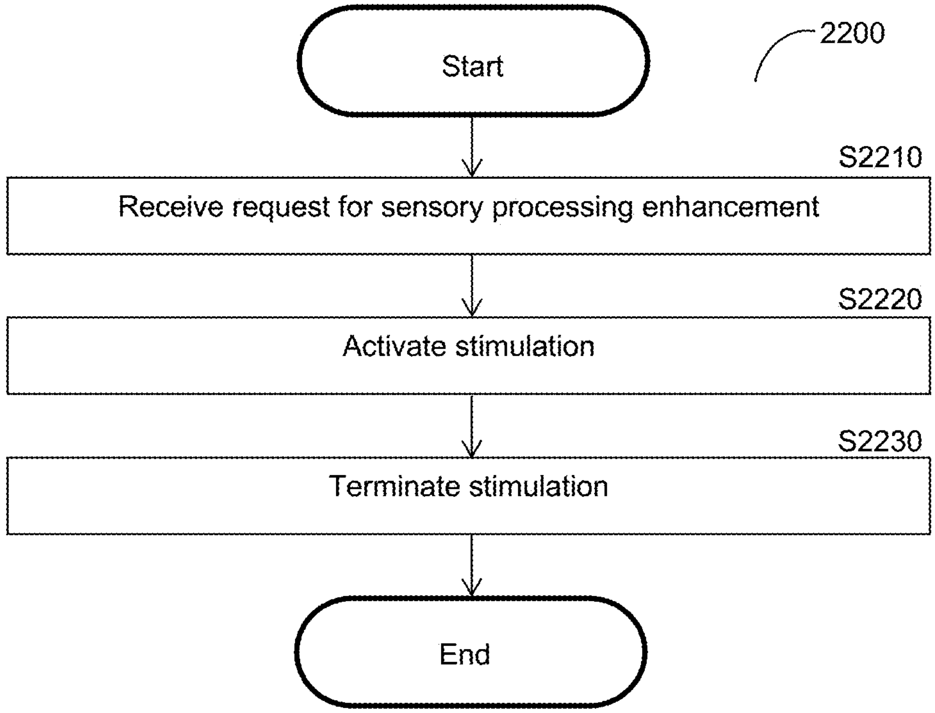
FIG. 22 is a flowchart illustrating a method for vagus nerve stimulation according to an embodiment.

FIG. 22 is a flowchart 2200 illustrating a method for vagus nerve stimulation according to an embodiment. In an embodiment, the method is performed via the hardware layer 2000, FIG. 20. In a further embodiment, the device is a device as described in one or more of the disclosed embodiments.

At S2210, a request for sensory processing enhancement is received. The request may be received, for example, based on user inputs (e.g., inputs indicating a user request for sensory processing enhancement), based on an automated program (e.g., a program configured to detect hearing loss as described further below with respect to FIG. 23), and the like. In some embodiments, the request may further indicate a degree of stimulation to be applied. User inputs may be received, for example but not limited to, from a user device of the user (e.g., via a software application installed on the user device), or via one or more buttons or other physical components of the device. The request for sensory processing may further indicate timing, duration, or both, for the stimulation.

At S2220, stimulation is activated. In an embodiment, S2220 includes sending one or more signals including commands for stimulation to one or more components of the device configured to provide nerve stimulation. In particular, such components may be or may include one or more components (e.g., electrodes) configured to apply electrical currents to the user in order to stimulate sensory processing as discussed herein.

In an embodiment, the device is a device configured in accordance with one or more disclosed embodiments. In a further embodiment, the device is disposed on one or more arteries of the user. In yet a further embodiment, the device is disposed on a carotid triangle of a neck of the user. In any such embodiments, the device is configured for vagus nerve stimulation as described herein.

In an embodiment, the stimulation is delivered using an uninterrupted tonic stimulation pattern. As noted above, such a pattern may improve effects on sensory perception, for example as compared to a duty-cycled stimulation pattern or other alternating or fluctuating stimulation pattern. Such stimulation may be delivered to the vagus nerve in order to steadily activate the norepinephrine (NE) system in a manner that improves the ability of a brain of the user to accurately process sensory information.

In an embodiment, stimulation is applied using a continuous stimulation pattern for a time period between 1 and 12 hours. In a further embodiment, a maximum length of time of quiescence is 10 seconds during the time period in which the continuous stimulation pattern is applied. That is, the maximum duration of any period of inactive time (i.e., time in which pulses are not being emitted) during the stimulation is 10 seconds. In another embodiment, such a maximum length of time of quiescence is 100 milliseconds during the time period in which the continuous stimulation pattern is applied.

At S2230, a trigger for ceasing sensory processing enhancement is detected. Such a trigger may be or may include, but is not limited to, passage of a predetermined period of time since beginning enhancement, passage of a duration of time indicated in the request, an end of detection of sensory signals, a combination thereof, and the like.

Figure 23:
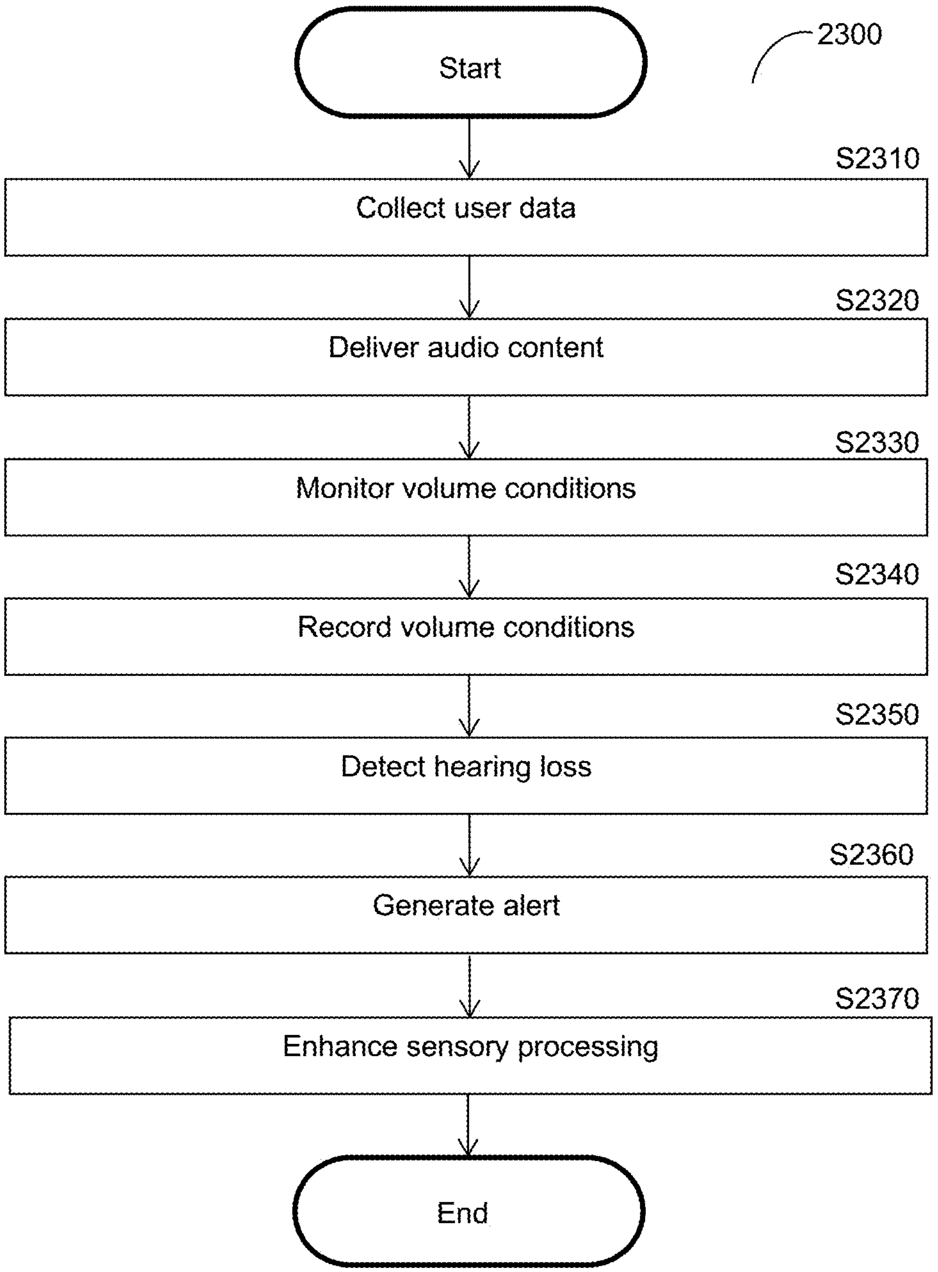
FIG. 23 is a flowchart illustrating a method for detecting hearing loss according to an embodiment.

FIG. 23 is a flowchart 2300 illustrating a method for detecting hearing loss according to an embodiment. In an embodiment, the method is performed via the user device 2100, FIG. 21. In a further embodiment, the device is a device as described in one or more of the disclosed embodiments.

At optional S2310, data is collected about a subject such as a user for which hearing loss is to be detected. Such data includes data which may be relevant to hearing loss and may include, but is not limited to, age, weight, sex, geographic location, average mobility, frequency of social interaction, combinations thereof, and the like. In a further embodiment, such data may be received as user inputs from a user device (e.g., a smartphone or tablet computer) of the user. Alternatively, such user data may be stored in a database, and S2310 may include retrieving the user data.

In some embodiments, the user data may include medical history information such as, but not limited to, whether the user has hearing loss which has been diagnosed. Information about existing hearing loss may be utilized to tailor the hearing loss detection in order to detect further hearing loss and to ignore previously diagnosed hearing loss for purposes of detection. That is, even if the process would result in diagnosing hearing loss for a normal user, changes in volume for a user who has already been diagnosed with hearing loss may not be detected as hearing loss unless the change in volume is indicative of further hearing loss than a baseline level established for the user (e.g., as determined by deviation above a predetermined threshold for a mean or otherwise representative value, or using a machine learning model trained based on data for the user).

At S2320, audio content is delivered. In an embodiment, delivering the audio content includes sending audio data for projection (e.g., via one or more speakers, headphones, or other devices or components configured to emit sound). In some embodiments, the audio data is sent to a device configured to modulate (i.e., control the volume of) sound to be projected, and that device may modify the volume prior to sending to a destination (e.g., the speaker, headphones, or other component through which the audio content will be projected).

At S2330, volume conditions are monitored. In an embodiment, the volume conditions include volume settings of the device at different points in time. In some embodiments, the volume is sampled periodically (e.g., every minute, every few minutes, every hour, etc.) at predetermined intervals. In a further embodiment, monitoring the volume conditions includes detecting when audio is being projected and sampling the volume during times when audio is being projected.

In an embodiment, the volume conditions are monitored in order to detect changes in volume preference (e.g., in scalar volume, average volume per month, peak volume used, etc.), for example, volume preference as reflected in choices of volume made by a user. In such an embodiment, detected changes may act as triggers to record volume conditions at the time of the detection of the change. In a further embodiment, a change in volume preference may be detected when a difference between an average or otherwise representative volume is above a predetermined threshold. In another embodiment, one or more machine learning models (e.g., support vector machines) may be trained based on training volume data for the user in order to train the machine learning models to detect volume levels that are abnormal or otherwise deviate from historical volume levels for the user. Moreover, in some embodiments, different machine learning models may be trained for the user, for example, machine learning models corresponding to respective devices, speakers, types of content, and the like, for volumes selected by the user. Monitoring for changes may allow for only recording changes in volume preferences for audio already being perceived for other purposes, which in turn may reduce the amount of data needed to be stored and processed in order to detect hearing loss as described herein and remove need for in-person patient visits for auditory testing to catch diagnosis of hearing loss.

In a further embodiment, devices for which audio is being projected are monitored in order to detect changes in user devices being used for projecting audio. In yet a further embodiment, changes in user devices which accompany changes in volume preference (e.g., which occur within a predetermined threshold period of time of a change in volume) may be utilized to determine that the change in volume is not caused by hearing loss. For example, a change in user devices which accompany change in volume preference may result in the change in volume being dismissed or otherwise not being recorded. In such embodiments, the type of device, the type of speaker, or both, may be logged. Such logging may be utilized to aid in identifying changes in volume preference for different devices, speakers, or combinations thereof (i.e., as reflected by volume choices made by users when different devices, speakers, or combinations of devices and speakers are being used).

In an embodiment, the volume conditions include a volume of an original signal sent for projection (e.g., for projection via a speaker) and a volume (e.g., amplitude) of the signal delivered to the speaker. In such embodiments, the monitored volume conditions effectively represent information including an amplitude of an original audio signal (e.g., an amplitude of a digital audio signal sent to a device which modulates amplitude of signals delivered to a speaker), a digital volume of the device which modulates amplitude of signals delivered to the speaker, and volume-related properties of the speaker. Monitoring both volume of an original signal and volume delivered to a speaker may allow for determining whether volume of the original signal has increased or has been boosted by the device which modulates the volume of data delivered to the speaker, which in turn may allow for determining whether the volume was boosted because the original signal was low (e.g., amplitude below a threshold).

In another embodiment, the volume conditions further include a noise level of an environment around the user (e.g., an environment around the speaker or headphones which project the audio content). In some embodiments, the noise level of the speaker is also recorded in addition to that of the environment. Such noise level values may be utilized to determine relative sound pressure value, which in turn may be utilized to further improve detection of hearing loss. In this regard, it is noted that noise in an environment may cause a user to increase volume even when the user is not experiencing hearing loss such that noise level may help in more accurately detecting whether the user has hearing loss. In a further embodiment, the noise level may be determined by accessing a microphone of the device or otherwise a microphone deployed in an environment of the user and obtaining audio recordings from that microphone. In yet a further embodiment, signal-to-noise ratios may be calculated based on a digital scalar volume level (e.g., as a signal level) and an amplitude-related measurement of sound level from the microphone (e.g., as a noise level).

Additionally or alternatively, in an embodiment, the volume conditions may include a type of device to which the audio is sent (e.g., a television, phone, smartphone, laptop computer, tablet computer, personal computer, etc.). In a further embodiment, the type of device may be defined with respect to a particular manufacturer, model, device identifier (e.g., serial number, device name, etc.), a combination thereof, and the like.

In this regard, it is noted that a device which modulates amplitude of audio being provided to a speaker may boost volume as compared to an original volume when the original signal is low, and that such boosting is typically not an indicator of hearing loss. In other words, when the volume is boosted because a signal was low for the speaker, such automatic boosting may be performed to compensate for potential signal loss rather than because a user is having difficulty hearing. If the original volume has increased (i.e., the volume before any such boosting), the cause of such an increase may be a user adjusting the volume upward because the user is having difficulty hearing. When the original volume has, on average, increased as compared to historical original volumes, hearing loss may be detected.

At S2340, the volume conditions are recorded. In an embodiment, the volume conditions are recorded as sets of volume conditions at different points in time (e.g., an original volume at a certain point in time and a subsequent volume delivered to a speaker within a threshold period of time). In a further embodiment, each set of volume conditions corresponds to a respective time and is recorded along with a timestamp indicating the time for which the volume conditions were captured, detected, or otherwise determined. In yet a further embodiment, each set of volume conditions is recorded along with a specific speaker to which the audio is being delivered with respect to that set of volume conditions (e.g., a computer speaker, an external speaker, headphones, etc.).

In some embodiments, the type of content being played is recorded for each set of volume conditions. The type of content may include, but is not limited to, categories of multimedia or audio content being delivered (e.g., music, video, phone or video call, etc.), certain types of content (e.g., song, movie, television, conversation, etc.), subsets of content types (e.g., news program or sitcom television show), specifically identified content (e.g., a particular song, movie, television show, television show episode, Internet video, etc.), an identifier of the source of the content (e.g., a caller identifier [ID] of a person to whom the user is speaking in a phone or video call), combinations thereof, and the like. Such information about the type of content being played may allow for more granularly tracking user volume preferences with respect to different kinds of content over time, which in turn may allow for more accurately identifying hearing loss. In this regard, it is noted that certain types of content may naturally be delivered with lower volume. As a non-limiting example, a news program may be naturally lower volume than a comedy special, or certain callers may naturally speak louder than others. Accordingly, comparing volume for like content over time allows for more accurately identifying whether the user is adjusting volume in response to certain content being naturally lower volume or because the user is experiencing effects of hearing loss.

In an embodiment, the volume conditions are recorded in a central repository. Such a central repository may be a storage which is accessible to multiple user devices and which may store volume conditions recorded by those user devices. Accordingly, recording the volume conditions may allow for tracking volume across different devices in order to provide a more comprehensive demonstration of volume preferences of the user over time. In some implementations, the database in which the volume conditions are recorded is stored locally within a user device performing the method of FIG. 23. In other implementations, the database may be stored remotely (e.g., in a server of a cloud computing environment) and accessed via one or more networks.

In a further embodiment, the central repository may include data of various users stored in a standardized format (e.g., as time series vectors for the same types of data for different users). Such data may be used, for example, initially until at least a predetermined amount of data specific to the user has been collected in order to allow for tailoring hearing loss detection to the user's habits and preferences. As noted above, data from individuals with previously diagnosed hearing loss may be utilized for hearing loss detection, for example, by initially utilizing data of diagnosed users' volume preference and extrapolating to other users with similar demographics and volume preferences who have the same condition or a similar degree of hearing loss (e.g., within a predetermined threshold of the user's hearing loss).

In yet a further embodiment, the volume data to be recorded is anonymized for storage in the central repository. The anonymization may be utilized to preserve privacy rights. Over time, the anonymized data, collected across users, allows for creating a distribution of known population values over time. Such known population values may be utilized to detect hearing loss using baselines for different devices, conditions (e.g., degree of hearing loss), demographics (e.g., as defined based on user data as discussed with respect to S2310), combinations thereof, and the like.

In some embodiments, the volume values may be normalized or otherwise standardized before being recorded. As a non-limiting example, digital scalar volume values may be standardized relative to respective background noise levels among the same sets of volume conditions.

At S2350, hearing loss is detected based on the recorded volume conditions. In an embodiment, when one or more most recent volume levels (e.g., values of amplitude) are more than a threshold above an average or otherwise baseline level (e.g., a baseline level for the user or an average level across users), then hearing loss is detected. Further, as discussed above, volume levels may be analyzed with respect to the type of content, user data, the component projecting the content, combinations thereof, and the like. As a non-limiting example, if a volume level is higher than a mean value plus 3 standard deviations based on historical volume levels, that volume level may be determined to be indicative of hearing loss and hearing loss is detected. In some embodiments, other volume conditions may be utilized to dismiss, ignore, or otherwise determine that the presence of certain volume levels are not to be detected as hearing loss. As a non-limiting example, In some embodiments, potential hearing loss may be analyzed with respect to a moving average. In a further embodiment, sets of volume conditions may be separated into time windows of equal length, where sets of volume conditions are organized into groups corresponding to time windows including their respective timestamps. An average or otherwise representative volume value may be determined for each time window, and each set of volume conditions may be analyzed with respect to the representative volume value for the respective time window. Moreover, in some embodiments, hearing loss may be detected when a threshold number of consecutive time windows include volume levels which are indicative of hearing loss (e.g., the most recent four time windows including such values).

In some embodiments, the representative values used to detect hearing loss may be or may include peak or otherwise maximum volume levels (e.g., the highest volume level within a given timeframe). In such embodiments, when the maximum volume level within a given time window exceeds a threshold (e.g., more than 2 standard deviations above an average maximum time value across previous time windows), hearing loss is detected. Other representative values may be or may include, but are not limited to, root mean square level, weighted measurements which take into account frequencies (e.g., frequencies which can be picked up by the human ear), combinations thereof, and the like.

In some embodiments, the hearing loss may be detected by applying one or more change point detection algorithms such as, but not limited to, Bayesian changepoint detection, Pettitt's test, cumulative sum control charts, and the like.

It should be noted that hearing loss is described as being determined based on average, maximum, or other representative values, but that other factors may be accounted for without departing from the scope of the disclosure. Such factors may include, but are not limited to, slope, acceleration, and the like.

At optional S2360, an alert is generated based on the detected hearing loss. The alert may indicate, for example but not limited to, the fact that hearing loss has been detected, the volume conditions that led to detection of hearing loss, a timestamp or time period for which the hearing loss was detected, the user for which hearing loss was detected, combinations thereof, and the like. In a further embodiment, S2360 includes generating a notification to be displayed on the user device or otherwise sent for viewing by the user. Alternatively or additionally, an alert may be sent to another program, for example, a health tracker application of the user.

At optional S2370, one or more treatments are applied based on the detected hearing loss. The treatments may be or may include, but are not limited to, enhancing sensory processing (e.g., utilizing one or more devices as described herein), modulating volume (e.g., via an audio modulator such as, but not limited to, a hearing aid, an audio modulator configured to control a speaker, both, and the like), prescribing one or more hearing exercises (e.g., via a software application of a user for which the hearing loss was detected), prescribing a surgery, prescribing earwax removal, prescribing gene or stem cell therapy, prescribing one or more vitamins or supplements, combinations thereof, and the like.

In an embodiment, S2370 includes modulating audio via one or more audio modulators. In a further embodiment, the audio modulator may be a hearing aid or other device worn by the user (either disposed invasively in the user or non-invasively on the user) for which the hearing loss was detected, and applying the treatment may include sending a control signal to the hearing aid in order to cause the hearing aid to modulate volume for the user so as to amplify volume for the user. In another embodiment, the audio modulator may be an audio modulator of one or more speakers (e.g., a speaker of a telephone, television, computer, external speaker, and the like) configured to modulate audio projected by those speakers. In some further embodiments, modulating the audio further includes causing the audio modulator to perform background noise suppression based on the detected hearing loss.

In an embodiment, S2370 includes enhancing sensory processing of the user based on the detected hearing loss. In an embodiment, enhancing sensory processing of the user includes applying an electrical current in order to stimulate a vagus nerve of the user. To this end, in a further embodiment, enhancing the sensory processing of the user includes activating or otherwise causing activation of a device in accordance with one or more of the disclosed embodiments. As discussed herein, such a device may be deployed on one or more arteries of the user and, in particular, disposed on a carotid triangle of a user's neck. Such devices may be configured to provide vagus nerve stimulation as described herein. The sensory processing of the user may be enhanced in order to compensate for the hearing loss. In some embodiments, S2370 includes determining a degree of stimulation based on a degree of hearing loss and enhancing sensory processing of the user accordingly (e.g., by sending a signal to the device indicating a degree to which the device should provide stimulation).

It should be noted that FIG. 23 illustrates the process as a single iteration, but that the process may be performed repeatedly or continuously without departing from the scope of the disclosure. Moreover, the method of FIG. 23 is described with respect to a single user device for simplicity, but that the method of FIG. 23 may, in at least some embodiments, be performed in a distributed manner across different user devices. In particular, steps such as delivering audio and monitoring volume settings may be performed individually by multiple user devices, and one or more of those user devices may detect hearing loss, make decisions regarding stimulating sensory processing, or both, based on data collected from any or all of the user devices in accordance with various disclosed embodiments.

In certain embodiments, a device as described herein may be designed for insertion into the ear of a subject. In this regard, the device may be adapted to fit into or on the ear of a subject to allow for positioning over the auricular branch. The components of the device may include, but are not limited to, a power source (e.g., a battery), a controller (e.g., a controller implemented as a microchip), a pair of electrodes, other components as discussed above, combinations thereof, and the like. More specifically, the controller may be configured to apply current using electricity from the power source to the pair of electrodes using a continuous biphasic pulse as described herein in order to enhance sensory processing via auricular stimulation of the vagus nerve.

In an embodiment, the stimulation intensity used for auricular stimulation described as follows is a different value of intensity than that for cervical stimulation (i.e., stimulation via nerves of the cervical plexus such as for stimulation via the carotid triangle as discussed above). In an embodiment, the stimulation intensity used for auricular stimulation is between 0.5 and 4 ma. In a further embodiment, the stimulation intensity used for auricular stimulation is 2 mA.

To this end, in an embodiment, a device is shaped to fit within an exterior facing side of the cymba concha of an ear of a subject. In this regard, it has been identified that the tissue of the cymba concha of the ear is the auricular region which is most densely innervated by the vagus nerve. Accordingly, the cymba concha provides a location within the ear which may be utilized to improve effectiveness of vagus nerve stimulation, to require lower amounts of current to achieve comparable levels of stimulation, both, and the like. Thus, at least some disclosed embodiments utilizing auricular stimulation include a device designed to be placed at least partially within the cymba concha in order to apply one or both electrodes to this location within the ear.

Figure 24:
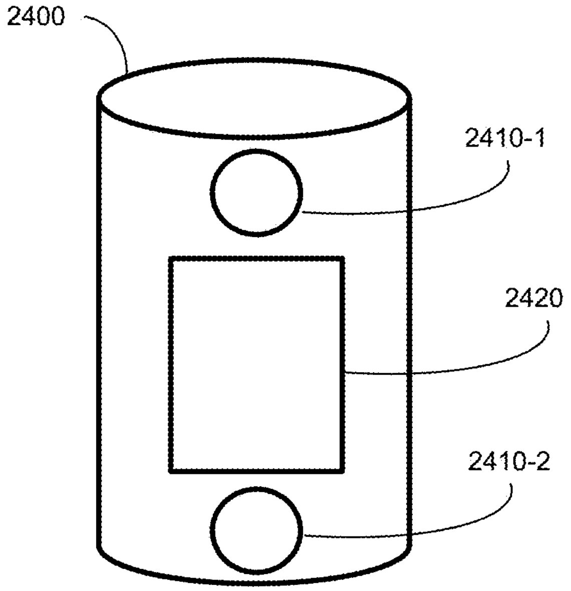
FIG. 24 is a diagram illustrating a device adapted for placement in the ear according to an embodiment.

A device which may be utilized for insertion into the cymba concha is now described with respect to FIG. 24. FIG. 24 is a diagram illustrating a device 2400 adapted for placement in the ear according to an embodiment.

As depicted in FIG. 24, the device 2400 includes a pair of electrodes 2410-1 and 2410-2 as well as an adhesive patch 2420. The pair of electrodes 2410-1 and 2410-2 may be utilized to deliver an electrical current as described herein, and in particular to provide auricular stimulation of the vagus nerve by disposing the device within a cymba concha of an ear of a subject. The adhesive patch 2420 may be utilized to adhere the device 2400 to the ear and, in particular, to adhere the device 2400 to a wall of the cymba concha.

As depicted in FIG. 24, in an embodiment, the device 2400 has a cylindrical shape, although other shapes may be utilized in at least some embodiments. In a further embodiment, the device 2400 has dimensions of roughly 1 to 3 centimeters in length and 0.5 to 1 centimeter in diameter.

Although not depicted in FIG. 24, the device 2400 may include components such as a power source (e.g., a battery) and a controller (e.g., a microchip) as discussed herein. Such components may be disposed inside of the device 2400, for example in a cavity defined within the device 2400 (not shown).

Figure 25:
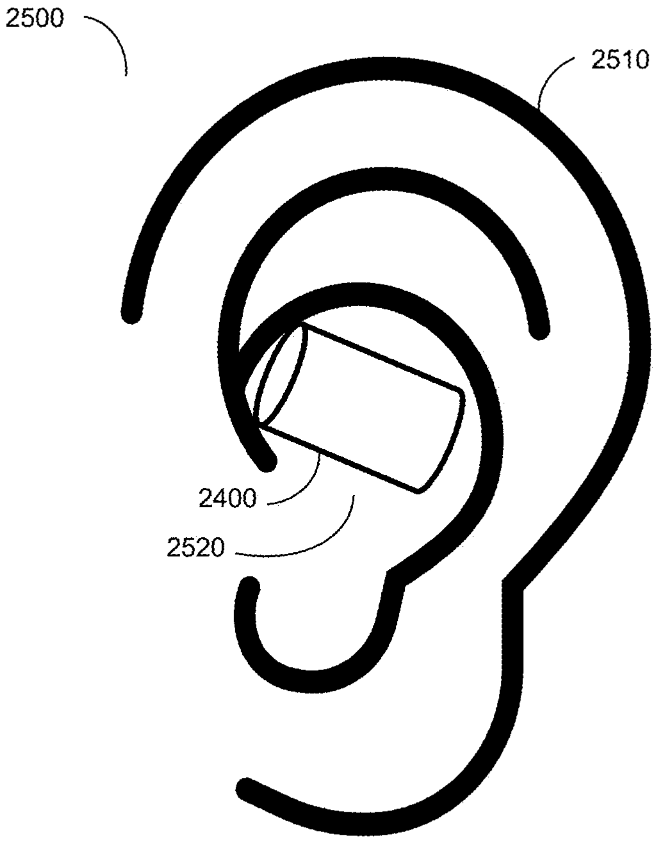
FIG. 25 is an illustration of a device placed in a cymba concha.

An example disposal of the device 2400 within a cymba concha is depicted in FIG. 25. FIG. 25 is an illustration 2500 of a device 2400 placed in a cymba concha 2520 of an ear 2510 of a subject.

In some embodiments, a first electrode (e.g., the electrode 2410-1, FIG. 24) of the device 2400 may be disposed in the cymba concha, and a second electrode (e.g., the electrode 2410-2, FIG. 24) may be placed in a different location within the ear. A non-limiting example implementation demonstrating such a placement is depicted in FIG. 26.

Figure 26:
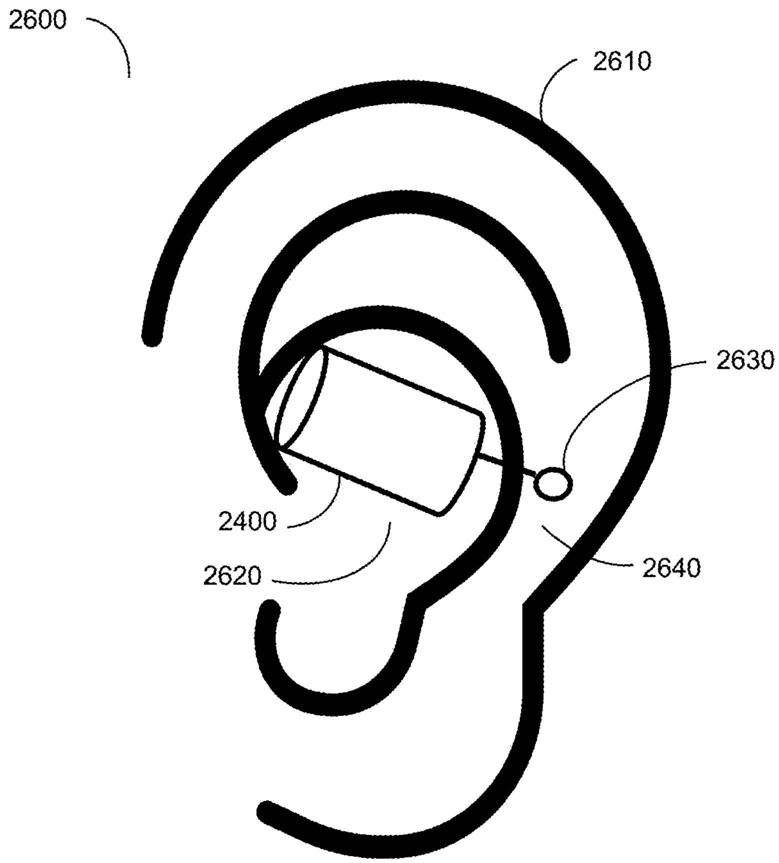
FIG. 26 is an illustration of a device placed in a cymba concha with an electrode placed in an adjacent portion of the ear.

FIG. 26 is an illustration 2600 of the device 2400 placed in a cymba concha 2620 of an ear 2610 of a subject. As depicted in FIG. 26, the device 2400 has an electrode 2630 which is disposed in a different location 2640 of the ear 2610. The location 2640 depicted in FIG. 26 is on a side of the ear 2610 which is directly opposite the cymba concha 2620, although different locations may be utilized in at least some disclosed embodiments.

In some embodiments, components such as a power source and a controller may be contained in a separate component such as an enclosure which is not disposed in the device 2400. A non-limiting example of such an implementation is now described with respect to FIGS. 27 and 28.

Figure 27:
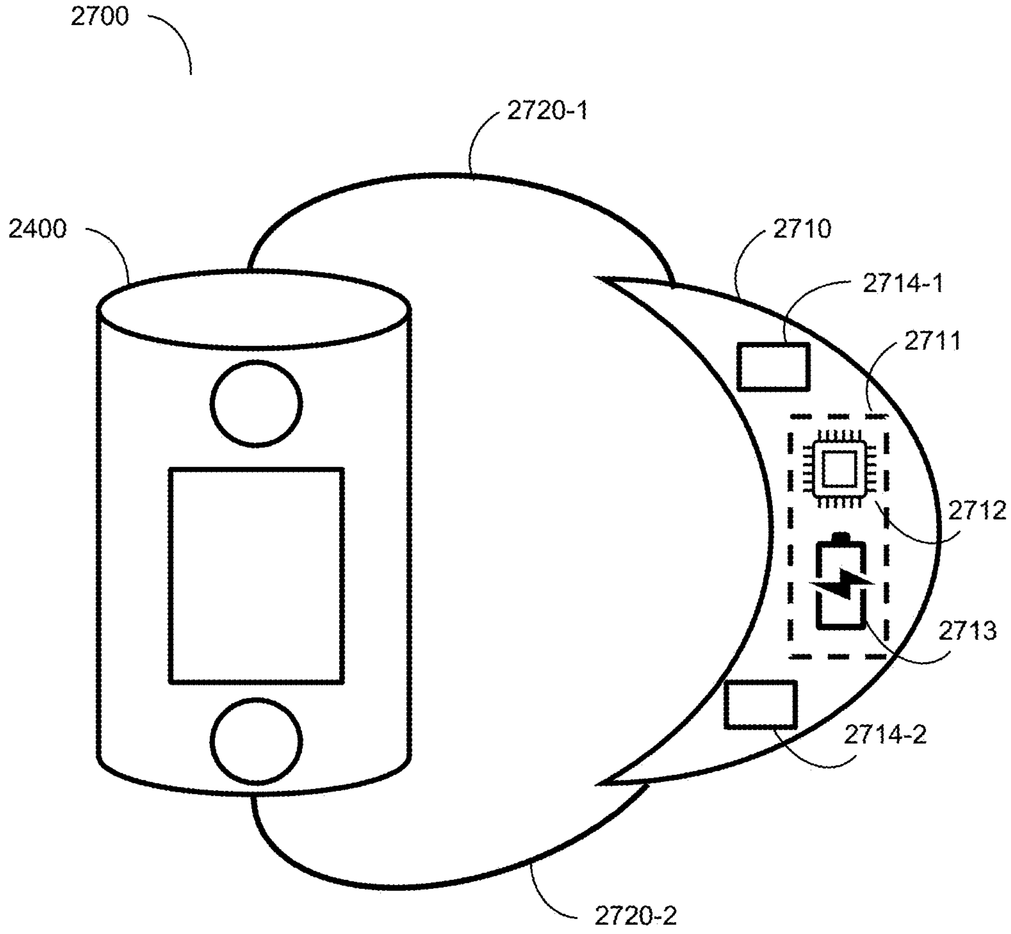
FIG. 27 is an illustration of a device utilizing a controller and power source stored in a separate enclosure.
Figure 28:
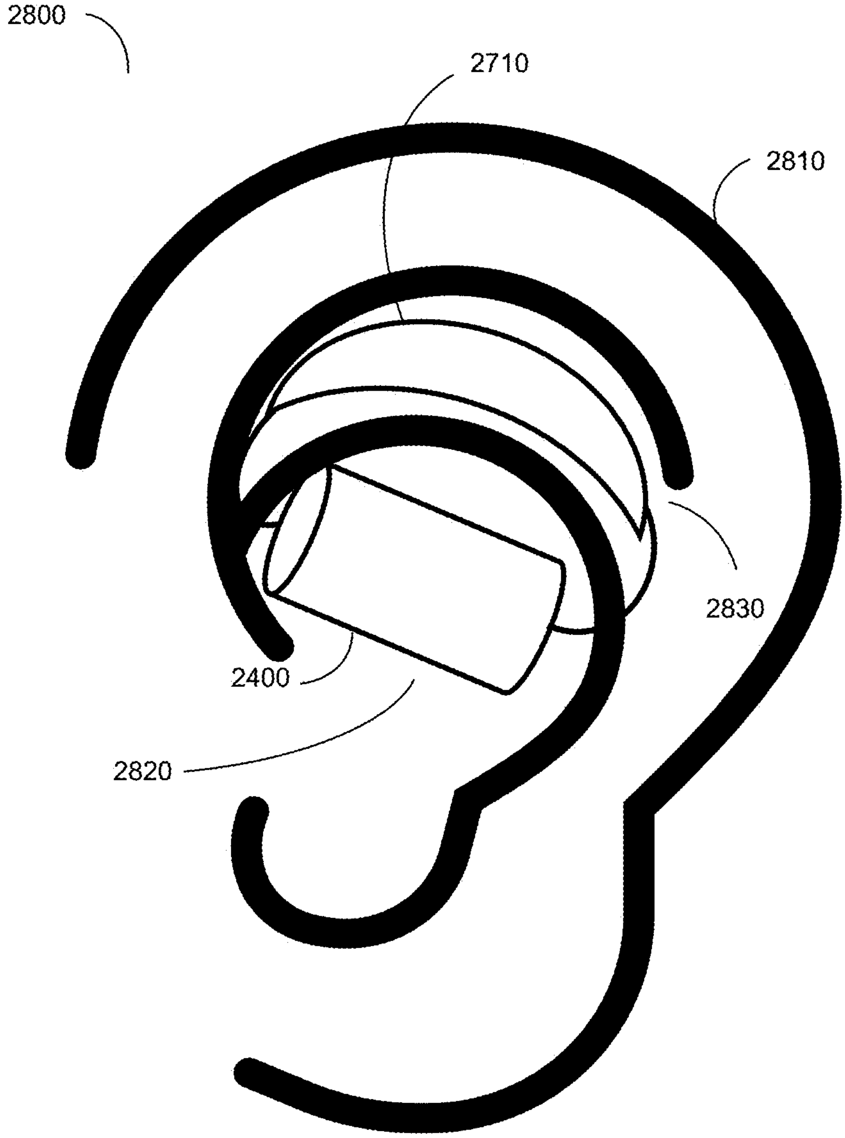
FIG. 28 is an illustration of a device disposed in a cymba concha with an enclosure disposed in a fossa triangularis.

FIG. 27 is an illustration 2700 of the device 2400 utilizing a controller 2712 and a power source 2713 stored in a separate enclosure 2710 according to an embodiment. As depicted in FIG. 27, the device 2400 is electrically connected to the enclosure 2710 via wires such as, but not limited to, wire leads 2720-1 and 2720-2. The enclosure 2710 has defined therein an internal cavity 2711 (represented by broken lines for illustrative purposes) in which the controller 2712 and the power source 2713 are disposed. The enclosure 2710 further has adhesive patches 2714-1 and 2714-2, which may be utilized to adhere the enclosure 2710, for example, to a wall of a fossa triangularis of an ear of a subject (e.g., as depicted in FIG. 28). It should be noted that two adhesive patches 2714 are depicted in FIG. 27 for example purposes only, but that other numbers of adhesive patches as well as adhesive patches of different shapes, relative sizes, or both, than those depicted in FIG. 27, may be utilized in accordance with at least some embodiments.

FIG. 28 is an illustration 2800 of the device 2400 disposed in a cymba concha 2820 of an ear 2810 of a subject with the enclosure 2710 disposed in a fossa triangularis 2830 of the ear 2810.

In some embodiments (not shown), a device may include both a first stimulation patch for stimulation at the carotid triangle location of the vagus nerve and a second stimulation patch for stimulation at an auricular location of the vagus nerve (e.g., the cymba concha) in order to allow for concurrent stimulation of both sites. Alternatively, two devices may be utilized, with each device being designed at a respective location among the carotid triangle location and one or more locations within the ear.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

At least some embodiments disclosed herein can be implemented as hardware, firmware, software, or any combination thereof. Moreover, the software may be implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for addressing hearing loss, comprising:

monitoring volume conditions of at least one device in order to detect a plurality of changes in volume, wherein a volume of each of the at least one device is controlled by a subject;

detecting hearing loss of the subject based on the monitored volume conditions; and applying a treatment to the subject when the hearing loss has been detected, wherein applying the treatment to the subject includes applying an electrical current in order to stimulate a vagus nerve of the subject, wherein applying the electrical current in order to stimulate a vagus nerve of the subject further comprises:

sending control signals in order to control the electrical current delivered from a power source to a pair of electrodes in a continuous biphasic stimulation pattern, wherein the pair of electrodes is spaced such that the pair of electrodes applies a current to stimulate a vagus nerve of the subject using a current delivered from the power source when the pair of electrodes is disposed along a carotid triangle of a neck of the subject.

2. The method of claim 1, wherein applying the treatment to the subject includes sending a control signal to an audio modulator, wherein the control signal causes the audio modulator to alter an audio modulation for at least one of the at least one device based on the detected hearing loss.

3. The method of claim 2, wherein the control signal further causes the audio modulator to perform background noise suppression based on the detected hearing loss.

4. The method of claim 1, wherein the at least one device is at least one first device, wherein the monitored volume conditions for each device include a volume of a signal sent to a second device configured to modulate amplitude and a volume of a signal sent from the second device to a speaker.

5. The method of claim 1, wherein the volume conditions are monitored with respect to choices of volume made by the subject.

6. The method of claim 1, wherein detecting the hearing loss further comprises:

applying at least one machine learning model to at least a portion of the monitored volume conditions, wherein each machine learning model is trained using a respective set of training volume data for the subject, wherein each machine learning model is trained to detect volume levels that deviate from historical volume levels for the subject.

7. The method of claim 6, wherein the at least one machine learning model includes a support vector machine.

8. The method of claim 6, wherein each of the at least one machine learning model corresponds to a respective device of the at least one device, wherein the respective set of training volume data used to train each of the at least one machine learning model is a set of volume data for the corresponding device of the machine learning model.

9. The method of claim 1, further comprising:

recording the monitored volume conditions with respect to a plurality of device types, wherein the hearing loss of the subject is detected based further on a type of device of each of the at least one device.

10. The method of claim 1, further comprising:

recording the monitored volume conditions with respect to a plurality of types of content being projected, wherein the hearing loss of the subject is detected based further on a type of content projected via each of the at least one device.

11. The method of claim 1, wherein the subject is a first subject, further comprising:

storing the monitored volume conditions in a storage which is accessible to a plurality of user devices of a plurality of subjects including the first subject, wherein the storage further stores volume conditions for the plurality of subjects, wherein the hearing loss is detected based on the volume conditions for the plurality of subjects.

12. The method of claim 1, wherein detecting the hearing loss further comprises:

separating the volume conditions into a plurality of time windows of equal length, wherein the volume conditions of each of the plurality of time windows include a plurality of volume values; and determining an average volume value for each of the plurality of time windows;

determining that the average volume value for at least a threshold number of consecutive time windows among the plurality of time windows is more than a threshold value above a baseline volume value, wherein the hearing loss is detected based on the determination that the average volume value for at least a threshold number of consecutive time windows among the plurality of time windows is more than a threshold value above a baseline volume value.

13. The method of claim 1, further comprising:

determining a degree of stimulation for the vagus nerve of the subject based on a degree of the hearing loss, wherein the electrical current is applied based on the determined degree of stimulation.

14. The method of claim 1, wherein an interelectrode distance between the pair of electrodes is between 4 and 5 centimeters.

15. The method of claim 14, wherein the interelectrode distance is 4 centimeters.

16. The method of claim 1, wherein the continuous biphasic stimulation pattern utilizes a plurality of pulses, wherein each pulse is less than one millisecond in length.

17. The method of claim 1, wherein the continuous stimulation pattern includes a plurality of pulses with a square biphasic waveform having two phases.

18. The method of claim 17, wherein each of the two phases of the square biphasic waveform is 100 milliseconds in length.

19. The method of claim 1, wherein the continuous biphasic stimulation pattern utilizes a plurality of pulses delivered at a frequency between 15 and 60 Hertz.

20. The method of claim 19, wherein the plurality of pulses is delivered at a frequency of 30 Hertz.

21. The method of claim 19, wherein the plurality of pulses is delivered at a frequency of 45 Hertz.

22. The method of claim 1, wherein the continuous biphasic stimulation pattern includes an asymmetric biphasic waveform.

23. The method of claim 1, wherein the electrical current delivered from the power source of the pair of electrodes in the biphasic stimulation pattern is initially delivered at a first current level and then incrementally increased from the first current level to a second current level.

24. The method of claim 23, wherein the first current level is 5 milliamps.

25. The method of claim 23, wherein the second current level is between 7 and 12 milliamps.

26. The method of claim 23, wherein the second current level is at most 60 milliamps.

27. The method of claim 1, wherein applying the electrical current in order to stimulate a vagus nerve of the subject further comprises:

sending control signals in order to control the electrical current delivered from a power source to a pair of electrodes in a continuous biphasic stimulation pattern, wherein the pair of electrodes is spaced such that the pair of electrodes applies a current to stimulate a vagus nerve of the subject using a current delivered from the power source when the pair of electrodes is disposed within a cymba concha of an ear of the subject.

28. The method of claim 27, wherein the continuous biphasic stimulation pattern has a stimulation intensity between 0.5 and 4 milliamps.

29. The method of claim 28, wherein the stimulation intensity of the continuous biphasic stimulation pattern is 2 milliamps.

30. A non-transitory computer readable medium having stored thereon instructions for causing a processing circuitry to execute a process, the process comprising:

monitoring volume conditions of at least one device in order to detect a plurality of changes in volume, wherein a volume of each of the at least one device is controlled by a subject;

detecting hearing loss of the subject based on the monitored volume conditions; and applying a treatment to the subject when the hearing loss has been detected, wherein applying the treatment to the subject includes applying an electrical current in order to stimulate a vagus nerve of the subject, wherein applying the electrical current in order to stimulate a vagus nerve of the subject further comprises:

sending control signals in order to control the electrical current delivered from a power source to a pair of electrodes in a continuous biphasic stimulation pattern, wherein the pair of electrodes is spaced such that the pair of electrodes applies a current to stimulate a vagus nerve of the subject using a current delivered from the power source when the pair of electrodes is disposed along a carotid triangle of a neck of the subject.

31. A system for addressing hearing loss, comprising:

a processing circuitry; and a memory, the memory containing instructions that, when executed by the processing circuitry, configure the system to:

monitor volume conditions of at least one device in order to detect a plurality of changes in volume, wherein a volume of each of the at least one device is controlled by a subject;

detect hearing loss of the subject based on the monitored volume conditions; and apply a treatment to the subject when the hearing loss has been detected, wherein the system is further configured to apply an electrical current in order to stimulate a vagus nerve of the subject, wherein the system is further configured to:

send control signals in order to control the electrical current delivered from a power source to a pair of electrodes in a continuous biphasic stimulation pattern, wherein the pair of electrodes is spaced such that the pair of electrodes applies a current to stimulate a vagus nerve of the subject using a current delivered from the power source when the pair of electrodes is disposed along a carotid triangle of a neck of the subject.

32. The system of claim 31, wherein the system is further configured to:

apply at least one machine learning model to at least a portion of the monitored volume conditions, wherein each machine learning model is trained using a respective set of training volume data for the subject, wherein each machine learning model is trained to detect volume levels that deviate from historical volume levels for the subject.

33. The system of claim 31, wherein the system is further configured to:

determine a degree of stimulation for the vagus nerve of the subject based on a degree of the hearing loss, wherein the electrical current is applied based on the determined degree of stimulation.

* * * * *